United States Patent
Yi et al.

(10) Patent No.: US 11,869,632 B2
(45) Date of Patent: Jan. 9, 2024

(54) METHOD AND SYSTEM FOR ANALYZING SEQUENCES

(71) Applicant: Genome Insight Technology, Inc., Daejeon (KR)

(72) Inventors: Kijong Yi, Daejeon (KR); Young Seok Ju, Daejeon (KR)

(73) Assignee: Genome Insight Technology, Inc., Daejeon (KR)

( * ) Notice: Subject to any disclaimer, the term of this patent is extended or adjusted under 35 U.S.C. 154(b) by 0 days.

(21) Appl. No.: 18/077,016

(22) Filed: Dec. 7, 2022

(65) Prior Publication Data
US 2023/0197199 A1   Jun. 22, 2023

(30) Foreign Application Priority Data

Dec. 16, 2021 (KR) .................. 10-2021-0180438
May 4, 2022 (KR) .................. 10-2022-0055514

(51) Int. Cl.
*G01N 33/48* (2006.01)
*G16B 30/10* (2019.01)
*G16B 40/00* (2019.01)

(52) U.S. Cl.
CPC .............. *G16B 30/10* (2019.02); *G16B 40/00* (2019.02)

(58) Field of Classification Search
None
See application file for complete search history.

(56) References Cited

U.S. PATENT DOCUMENTS

| | | |
|---|---|---|
| 2015/0066385 A1 | 3/2015 | Schnall-Levin et al. |
| 2015/0120208 A1 | 4/2015 | Park |
| 2020/0176081 A1 | 6/2020 | Jung et al. |
| 2020/0208195 A1 | 7/2020 | Jeong et al. |

FOREIGN PATENT DOCUMENTS

| | | |
|---|---|---|
| AU | 2019200163 B2 | 1/2019 |
| KR | 10-2015-0049749 A | 5/2015 |
| KR | 10-2017-0142871 A | 12/2017 |
| KR | 101867011 B1 | 6/2018 |
| KR | 102056583 B1 | 12/2019 |
| KR | 10-2020-0098189 A | 8/2020 |

OTHER PUBLICATIONS

Stranneheim, Henrik, et al. "Rapid pulsed whole genome sequencing for comprehensive acute diagnostics of inborn errors of metabolism." BMC genomics 15.1 (2014): 1-10.*
Loka et al. "Reliable variant calling during runtime of Illumina sequencing", Scientific Reports, www.nature.com/srep/ <http://www.nature.com/srep/>, pp. 1-8.
"Estimating Sequencing Coverage", Illumina, Technical Note: Sequencing, 2014, pp. 1-2.
Loka, "Advanced Strategies for Alignment-based Real-time Analysis and Data Protection in Next-Generation Sequencing", Freie University Berlin, Berlin, 2019, pp. 1-125.
Payne, Alexander et al. "Readfish enables targeted nanopore sequencing of gigabase-sized genomes." nature biotechnology 14 pages.

* cited by examiner

*Primary Examiner* — Anna Skibinsky
(74) *Attorney, Agent, or Firm* — Banner & Witcoff, Ltd.

(57) ABSTRACT

A method for analyzing sequences performed by one or more processors is provided, including aligning first sequence data generated at a first time point based on reference sequence data, in which the first time point is a time point after reading of a first read of a pair of paired-end reads is completed and at which a second read of the pair of paired-end reads is partially read, identifying a structural variant from the aligned first sequence data, and before reading the second read is completed, generating a first report including information on the identified structural variant.

20 Claims, 15 Drawing Sheets

| GENE | LOCATION | MUTATION | EARLY ANALYSIS TIME | RESULT | FALSE NEGATIVE RATE | FALSE POSITIVE RATE |
|---|---|---|---|---|---|---|
| EGFR | chr7:55191822 | c.2573T>G, p.L858R | 40 | POSITIVE | | 5% |
| KRAS | chr12:25245351 | c.34G>T, p.G12C | 40 | NEGATIVE | 40% | |

(a)

| GENE | LOCATION | MUTATION | EARLY ANALYSIS TIME | RESULT | FALSE NEGATIVE RATE | FALSE POSITIVE RATE |
|---|---|---|---|---|---|---|
| EGFR | chr7:55191822 | c.2573T>G, p.L858R | 150 + 40 | POSITIVE | | 1% |
| KRAS | chr12:25245351 | c.34G>T, p.G12C | 150 + 40 | NEGATIVE | 90% | |

| ANALYSIS TIME | 40 | 150 + 40 | 150 + 150 |
|---|---|---|---|
| TOTAL SEQUENCING AMOUNT | 250 GIGABASE | | |
| TARGET SEQUENCING AMOUNT | 30 GIGABASE | 158 GIGABASE | 250 GIGABASE |
| EXPECTED REACH | 10X | 47.5X | 75X |
| POINT MUTATION DETECTION SENSITIVITY | 93% | 99% | 99% |
| DETECTION SENSITIVITY AT 80% OF TUMOR CELL FRACTION | 90% | 95% | 97% |

FIG. 9

| RATIO OF TUMOR TUMOR CELLS IN SAMPLE(x) | AMOUNT NEEDED FOR EARLY ANALYSIS AT CYCLE 40 | AMOUNT NEEDED FOR EARLY ANALYSIS AT CYCLE 150+40 |
|---|---|---|
| $x \leq R1$ | 120 (900) | 100 (160) |
| $R1 < x \leq R2$ | 85 (637.5) | 72 (112) |
| $R2 < x \leq R3$ | 62 (465) | 52 (82) |
| $R3 < x \leq R4$ | 42 (315) | 36 (56) |
| $R4 < x$ | 33 (247) | 28 (44) |

FIG. 14

METHOD AND SYSTEM FOR ANALYZING SEQUENCES

CROSS-REFERENCE TO RELATED APPLICATION

This application claims priority under 35 U.S.C § 119 to Korean Patent Application No. 10-2021-0180438, filed in the Korean Intellectual Property Office on Dec. 16, 2021 and No. 10-2022-0055514, filed in the Korean Intellectual Property Office on May 4, 2022, the entire contents of which are hereby incorporated by reference.

TECHNICAL FIELD

The present disclosure relates to a method and system for analyzing sequences, and specifically, to a method and system for analyzing sequences which use partial sequence data to identify variants before analyzing the entire DNA sequences is completed, and provide an early report of the same.

BACKGROUND

In recent years, researches to elucidate genes related to human diseases have been actively carried out. In particular, the project that deciphers the genome that contains the human body's genetic information and creates a genetic map and analyze the same to thus predict the occurrence of human diseases are actively carried out.

The project can involve the task of comparing the sequence data of the test subject with the reference sequence data to identify a sequence of the test subject where the variant is occurring, and deriving a disease correlation for the test subject based on the identified sequence.

To implement the project fast, the Next-Generation Sequencing (NGS) technology is used. The NGS technology performs sequencing by synthesis through a synthesis of fragmented DNA (deoxyribonucleic acid) to generate large volumes of sequence data. For example, the NGS using the Illumina's sequencer reads the DNA fragments and an image file with the fluorescently labelled nucleotides is generated. The fluorescent material included in the image file is converted into sequence data that is a set of computer-readable letters, and the sequence data is aligned, or mapped, based on the reference sequence data. The aligned sequence data is compared with the reference sequence data, and the position and gene where the variant occurs are identified. The NGS can be classified into the targeted panel sequencing that sequences only the selected DNA of the region of interest, the whole genome sequencing that sequences the entire genome, etc.

Meanwhile, performing the whole genome sequencing through NGS technology takes a long time (e.g., about 45 hours or more) until the image file is acquired, and additional time is also required to read the fluorescent material included in the image file and convert it into sequence data, align the sequence data, and identify variants (i.e., variant calling).

Meanwhile, at the medical site, an emergency situation may occur in which a treatment plan must be established quickly based on a patient's genetic variant. For example, emergency situations may arise, such as a situation that urgently requires to select a targeted therapeutic agent, a situation that requires rapid bacterial identification to determine an antibiotic, etc. In these emergency situations, treatment plan is established based on the patient's genetic variant, but if it takes a long time for the sequencing, it can cause a delay in the establishment of the treatment plan in the emergency situations. Accordingly, there is a demand from the medical workers for more rapid sequencing.

SUMMARY

In order to solve one or more problems (e.g., the problems described above and/or other problems not explicitly described herein), the present disclosure provides a method for analyzing sequences, a computer program stored in a recording medium for analyzing sequences, and an apparatus (system) for analyzing sequences.

The present disclosure may be implemented in a variety of ways, including a method, a device (system), and/or a non-transitory computer-readable storage medium recording instructions.

A method performed by one or more processors may include aligning, based on reference sequence data, first sequence data generated at a first time point, wherein the first time point is a time point after reading of a first read of a pair of paired-end reads is completed and at which a second read of the pair of paired-end reads is partially read, identifying, the aligned first sequence data, a structural variant, and before reading of the second read is completed, generating a first report including information on the identified structural variant.

In addition, the method may further include before the aligning the first sequence data, aligning, based on the reference sequence data, second sequence data generated at a second time point, in which the second time point may be a time point at which the first read is partially read and before reading of the read is started, identifying, based on the aligned second sequence data, a point mutation, and generating a second report including information on the identified point mutation.

In addition, the method may further include before the generating the first report, identifying, based on the aligned first sequence data, a point mutation, wherein the first report may further include information on the identified point mutation.

In addition, the first time point may be a time point at which partially read sequence data of the second read is sufficient to be aligned with the reference sequence data.

In addition, the method may further include before the aligning the first sequence data, determining a target data amount for sequence production, and acquiring the first sequence data, wherein the first sequence data is generated by a sequencer inputted with an amount of a sample corresponding to the determined target data amount.

In addition, the determining the target data amount may include acquiring a ratio of tumor cells included in the sample to non-tumor cells included in the sample, and determining, based on at least one of the acquired ratio of tumor cells or an analysis time point, the target data amount, wherein the analysis time point may be either the first time point or a second time point being a time point at which the first read is partially read and before the reading of the second read is started.

In addition, the acquiring the ratio may include identifying, based on a disease type of a test subject, the ratio.

In addition, the determined target data amount may be an amount of data required for early reporting of a variant identification result, and a size of the acquired first sequence data may be a size corresponding to the determined target amount data.

In addition, the method may further include, after the determining the target data amount, outputting an amount of the sample corresponding to the determined target data amount.

In addition, the method may further include, before the aligning the first sequence data, aligning, based on the reference sequence data, second sequence data generated at a second time point, wherein the second time point may be a time point at which the first read is partially read and before reading of the read is started, and deferring, based on a failure associated with the aligning the second sequence data, an alignment operation associated with the second sequence data.

In addition, the reference sequence data may include a plurality of sub-regions, and wherein the deferring the alignment operation associated with the second sequence data may include calculating an alignment ratio, wherein the alignment ration may include a ratio of reads uniquely aligned to one sub-region to reads included in the second sequence data, and based on the calculated alignment ratio being less than a target alignment ratio, determining the failure associated with aligning the second sequence data.

In addition, the method may further include, after the deferring the alignment operation associated with the second sequence data, retrying an alignment of the second sequence data, wherein the retrying the alignment of the second sequence is based on: an additional nucleotide identifier being added to the second sequence data, and a number of the additional nucleotide identifiers added to the second sequence data reaching a predetermined threshold number.

In addition, the method may further include before the aligning the second sequence data, acquiring target variant information and determining, from an entire region associated with the reference sequence data, a sub-region associated with the target variant information, wherein the deferring the alignment operation associated with the second sequence data may include based on the second sequence data being not mapped to the determined sub-region, determining the failure associated with aligning the second sequence data.

In addition, the target variant information may be acquired based on disease information of a test subject.

In addition, the method may further include analyzing a whole genome sequencing result.

There may be provided a computer-readable non-transitory recording medium storing instructions that, when executed, cause: align, based on reference sequence data, first sequence data generated at a first time point, wherein the first time point is a time point after reading of a first read of a pair of paired-end reads is completed and at which a second read of the pair of paired-end reads is partially read, identify, based on the aligned first sequence data, a structural variant, and before reading of the second read is completed, generate a first report comprising information on the identified structural variant.

A system may include one or more processors, and memory storing instructions that, when executed by the one or more processors, cause the system to: align, based on reference sequence data, first sequence data generated at a first time point, wherein the first time point is a time point after reading of a first read of a pair of paired-end reads is completed and at which a second read of the pair of paired-end reads is partially read; identify, based on the aligned first sequence data, a structural variant; and before reading of the second read is completed, generate a first report comprising information on the identified structural variant.

Since the analyzing sequences can be performed based on partial marking data acquired during the process, without having to wait for the work to be completed by the sequencer, the client can be provided with a report including the analysis result at an early stage. Accordingly, the client can receive a report quickly, and quickly establish a treatment plan based on the variants included in the report.

Since the partial marking codes can be converted into nucleotide identifiers upon acquisition from the sequencer, compared to the related method having the subsequent processes in queue until all the marking codes are generated, the analysis time can be significantly reduced. In addition, since the conversion and alignment of the sequence data are performed simultaneously, the analyzing sequences can be performed more quickly.

A variant can be observed with respect to a designated region (target region) in the entire sequence data based on target variant information related to a disease of interest. Accordingly, a variant related to a disease of a test subject (e.g., a patient) can be reported more quickly during the process for analyzing sequences.

Processors or nodes included in the system are operated in parallel, so that the time for analyzing sequences can be further reduced.

The amount (ratio) of the test subject's sample to the total sample input to the sequencer can be determined based on at least one of a ratio of tumor cells in a sample of the test subject requiring emergency analysis input to the sequencer to non-tumor cells in the sample, a desired early analysis time point, and a cost required in proportion to the sequencing data output, and it can be controlled such that data corresponding to the determined amount of the sample can be processed in the sequencer. Accordingly, the sequencer can be operated more efficiently, and profits can be maximized.

The effects of the present disclosure are not limited to the effects described above, and other effects not described herein can be clearly understood by those of ordinary skill in the art (referred to as "ordinary technician") from the description of the claims.

BRIEF DESCRIPTION OF THE DRAWINGS

The above and other objects, features and advantages of the present disclosure would be described with reference to the accompanying drawings described below, where similar reference numerals indicate similar elements, but not limited thereto, in which:

FIG. 7 is a diagram illustrating a result of variant occurrence determination included in a first report and a second report;

FIG. 9 is an exemplary chart comparing each analysis time point (i.e. cycles 40, 190, and 300) in terms of expected sensitivity and sequencing amount;

FIG. 14 is a diagram illustrating the amount of data required for early analysis according to the ratio of the amount of DNA extracted from tumor cells to the amount of DNA extracted from non-tumor cells included in the sample.

DETAILED DESCRIPTION

Figure 1:
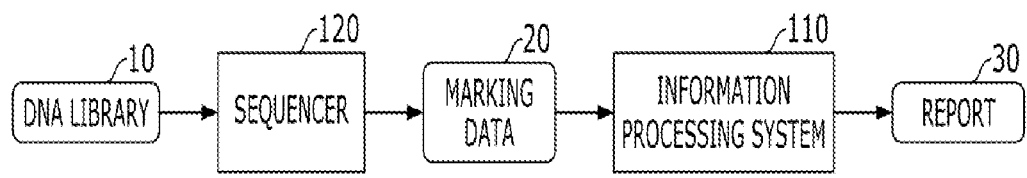
FIG. 1 is an exemplary diagram schematically illustrating an information processing system and its service providing environment.

Hereinafter, example details for the practice of the present disclosure will be described in detail with reference to the accompanying drawings. However, in the following description, detailed descriptions of well-known functions or configurations will be omitted if it may make the subject matter of the present disclosure rather unclear.

In the accompanying drawings, the same or corresponding components are assigned the same reference numerals. In addition, in the following description of various examples, duplicate descriptions of the same or corresponding components may be omitted. However, even if descriptions of components are omitted, it is not intended that such components are not included in any example.

Advantages and features of the disclosed examples and methods of accomplishing the same will be apparent by referring to examples described below in connection with the accompanying drawings. However, the present disclosure is not limited to the examples disclosed below, and may be implemented in various forms different from each other, and the examples are merely provided to make the present disclosure complete, and to fully disclose the scope of the disclosure to those skilled in the art to which the present disclosure pertains.

The terms used herein will be briefly described prior to describing the disclosed embodiment(s) in detail. The terms used herein have been selected as general terms which are widely used at present in consideration of the functions of the present disclosure, and this may be altered according to the intent of an operator skilled in the art, related practice, or introduction of new technology. In addition, in specific cases, certain terms may be arbitrarily selected by the applicant, and the meaning of the terms will be described in detail in a corresponding description of the embodiment(s). Therefore, the terms used in the present disclosure should be defined based on the meaning of the terms and the overall content of the present disclosure rather than a simple name of each of the terms.

As used herein, the singular forms "a," "an," and "the" are intended to include the plural forms as well, unless the context clearly indicates the singular forms. Further, the plural forms are intended to include the singular forms as well, unless the context clearly indicates the plural forms. Further, throughout the description, if a portion is stated as "comprising (including)" a component, it intends to mean that the portion may additionally comprise (or include or have) another component, rather than excluding the same, unless specified to the contrary.

Further, the term "module" or "unit" used herein refers to a software or hardware component, and "module" or "unit" performs certain roles. However, the meaning of the "module" or "unit" is not limited to software or hardware. The "module" or "unit" may be configured to be in an addressable storage medium or configured to play one or more processors. Accordingly, as an example, the "module" or "unit" may include components such as software components, object-oriented software components, class components, and task components, and at least one of processes, functions, attributes, procedures, subroutines, program code segments, drivers, firmware, micro-codes, circuits, data, database, data structures, tables, arrays, and variables. Furthermore, functions provided in the components and the "modules" or "units" may be combined into a smaller number of components and "modules" or "units", or further divided into additional components and "modules" or "units."

The "module" or "unit" may be implemented as a processor and a memory. The "processor" should be interpreted broadly to encompass a general-purpose processor, a central processing unit (CPU), a microprocessor, a digital signal processor (DSP), a controller, a microcontroller, a state machine, and so forth. Under some circumstances, the "processor" may refer to an application-specific integrated circuit (ASIC), a programmable logic device (PLD), a field-programmable gate array (FPGA), and so on. The "processor" may refer to a combination for processing devices, e.g., a combination of a DSP and a microprocessor, a combination of a plurality of microprocessors, a combination of one or more microprocessors in conjunction with a DSP core, or any other combination of such configurations. In addition, the "memory" should be interpreted broadly to encompass any electronic component that is capable of storing electronic information. The "memory" may refer to various types of processor-readable media such as random access memory (RAM), read-only memory (ROM), non-volatile random access memory (NVRAM), programmable read-only memory (PROM), erasable programmable read-only memory (EPROM), electrically erasable PROM (EEPROM), flash memory, magnetic or marking data storage, registers, and so on. The memory is said to be in electronic communication with a processor if the processor can read information from and/or write information to the memory. The memory integrated with the processor is in electronic communication with the processor.

In the present disclosure, a "system" may refer to at least one of a server device and a cloud device, but not limited thereto. For example, the system may include one or more server devices. As another example, the system may be configured with one or more cloud devices (e.g., a sequencer, etc.). As still another example, the system may include both the server device and the cloud device operating in conjunction with each other.

In addition, terms such as first, second, A, B, (a), (b), etc. are only used to distinguish a component from other components, and the essence, order, sequence, etc. of the component is not limited by the term.

In addition, in the following examples, if a certain component is stated as being "connected", "combined" or "coupled" to another component, it is to be understood that there may be yet another intervening component "connected", "combined" or "coupled between the two components, although the two components may also be directly connected or coupled to each other.

In addition, as used in the following examples, "comprise" and/or "comprising" does not foreclose the presence or addition of one or more other elements, steps, operations, and/or devices in addition to the recited elements, steps, operations, or devices.

Before describing various examples of the present disclosure, terms used will be described.

In the examples of the present disclosure, a "DNA library" refers to a set of prepared samples processed into a form suitable for sequencing. The DNA library may include countless DNA fragments acquired from cells of one or more test subjects.

In the examples of the present disclosure, a "DNA read" refers to a unit of genetic information data output as a result of a sequencer reading a DNA fragment, and the target length of the read is set constant in one run of sequencing process. The paired-end sequencing method outputs a pair of reads for each DNA fragment, and the pair of reads obtained from one DNA fragment represents sequences at each end of the DNA fragment, respectively. Each read may include one or more nucleotide identifiers.

In the examples of the present disclosure, a "marking code" may be a code related to a nucleotide included in a DNA fragment. In one example, the marking code may be image data. Indicating the marking code may involve use of the attribute of the marking code. According to some examples, for the attribute of the marking code, fluorescent materials that are distinguished from each other may be used. For example, a first marking code may be marked with a first fluorescent material representing adenine, and a second marking code may be marked as a second fluorescent material representing cytosine. As another example, a third marking code may be marked as a third fluorescent material representing guanine, and a fourth marking code may be marked as a fourth fluorescent material representing thymine.

In the examples of the present disclosure, "marking data" may be data including one or more marking codes. For example, the marking data may be an image file.

In the examples of the present disclosure, the "nucleotide identifier" may be a letter representing a nucleotide. For example, the nucleotide identifier may include "A" for adenine, "C" for cytosine, "G" for guanine, and "T" for thymine.

In the examples of the present disclosure, the "sequence data" may include one or more nucleotide identifiers. For example, the "sequence data" may include at least one read described above.

In the examples of the present disclosure, "sequence data alignment" may uniquely specify, among the sub-regions of the entire region (hereinafter referred to as "the entire reference region") associated with the reference sequence data, a sub-region in which target sequence data to be analyzed is positioned. That is, the sequence data alignment may refer to alignment of each read included in the sequence data in the sub-region. For example, throughout a sequencing operation, sequence data including a plurality of reads may be generated, while the alignment for each read included in the generated sequence data is performed simultaneously. Some of the reads included in the sequence data may not be aligned (mapped). In this case, the unaligned read may indicate that the read is not specific to a unique sub-region. For example, if a specific read is mapped to more than one sub-regions within the entire reference region, or if a specific read is not mapped to any sub-region, it may be determined that the specific read is not aligned.

In the examples of the present disclosure, a "variant" may be identified as a portion of the sequence of the sample to be analyzed, which is different from the reference sequence. In this example, the variant may include a variety/variant, a mutation, etc. In addition, the variant may refer to a phenomenon in which the sequence is added, changed, and/or deleted for a certain reason (e.g., DNA damage, replication error, etc.).

In the present disclosure, "instructions" may refer to a series of computer readable instructions grouped based on a function, and to a component of a computer program being executed by a processor.

Hereinafter, various examples of the present disclosure will be described in detail with reference to the accompanying drawings.

FIG. 1 is an exemplary diagram schematically illustrating an information processing system 110 and its service providing environment. A DNA library 10 including a DNA sample of a test subject may be generated. For example, cells from tissues and/or blood of the test subject (e.g., a human patient) to be analyzed are collected, and while being stored in a predetermined solution in a test tube, the cells are subjected to a preprocessing such as heating, centrifugation, etc., and through this, the DNA library 10 including countless DNA fragments acquired from the cells of the test subject can be generated.

The DNA library 10 may include DNA samples acquired from only one test subject, but generally, it may include DNA samples acquired from a plurality of test subjects. For example, a DNA sample generated from the cells of a first test subject and a DNA sample generated from the cells of a second test subject may be included in the DNA library 10 together. That is, sequencing operations of two or more test subjects may be simultaneously performed by a sequencer 120 at a time.

Typically, the total amount of DNA samples prepared in the form of the DNA library 10 and input to the sequencer 120 is fixed. If DNA samples of a plurality of test subjects are included in the DNA library 10 in equal amounts, the equal quantity of sequence data of each of the plurality of test subjects may be included in the sequence data output as a result of the sequencing. On the other hand, depending on purpose, the specific gravity of the DNA samples of certain test subjects of the DNA samples of the plurality of test subjects included in the DNA library 10 may be increased so as to increase the specific gravity of the sequence data of the certain test subjects in the sequence data output as a result of the sequencing. In other words, if the DNA sample of the first test subject is included in a greater specific gravity when preparing the DNA library 10, more data corresponding to the sequence of the first test subject may be acquired from the sequencer 120.

The DNA library may be loaded into the cartridge, and the cartridge may be loaded into the sequencer 120. In some examples, any method capable of loading the DNA library to the sequencer 120 may be used.

The sequencer 120 may identify a nucleotide type of each DNA fragment included in the DNA library 10 and generate marking data including a marking code corresponding to the identified nucleotide type. The sequencer 120 may identify one nucleotide included in each DNA fragment for every cycle, generate a marking code corresponding to the identified nucleotide, and additionally record the generated marking code in the marking data to update the marking data. The sequencer 120 may generate one image file representing the marking codes generated for all DNA fragments for every cycle. The marking data may be a set of image files generated for every cycle, and may be stored in a storage device that the information processing system 110 can access as will be described below.

The information processing system 110 may be a system for analyzing sequences. For example, the information processing system 110 may generate, at a time point when the marking codes of all cycles are not generated by the sequencer 120 (that is, when the entire sequencing operation is not completed), sequence data including a read corresponding to each DNA fragment included in the DNA library 10 based on some marking data 20 generated by the sequencer 120 A plurality of marking data 20 corresponding to the number of DNA fragments may be generated by the sequencer 120, and the information processing system 110 may generate sequence data including a plurality of reads corresponding in number to the DNA fragments. For example, if (n) number of DNA fragments (where n is a natural number) are included in the DNA library 10, the sequencer 120 may generate (n) number of marking data 20 in a specific cycle. The information processing system 110 may generate sequence data including (n) number of reads based on the (n) number of marking data 20.

In addition, the information processing system 110 may compare the partially converted sequence data with the reference sequence data, align the sequence data, and identify the variant of the test subject from the sequence data. The information processing system 110 may generate a report 30 including detailed information on the identified variant (e.g., variant occurrence position), information on accuracy of the variant occurrence determination, etc. and provide the report 30 to a client (e.g., a medical staff).

The information processing system 110 may convert the marking code into the nucleotide identifier in real time, or convert a plurality of marking codes into a plurality of nucleotide identifiers in a specified cycle.

Figure 2:
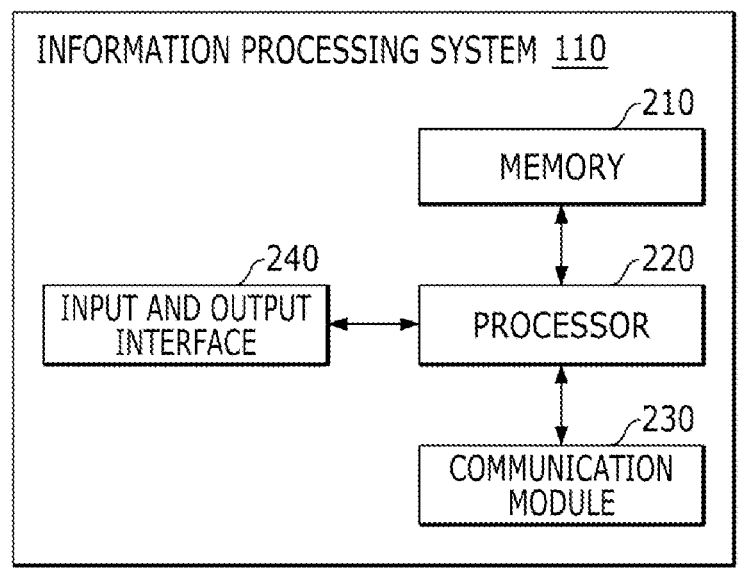
FIG. 2 is a block diagram illustrating an internal configuration of the information processing system.
Figure 3:
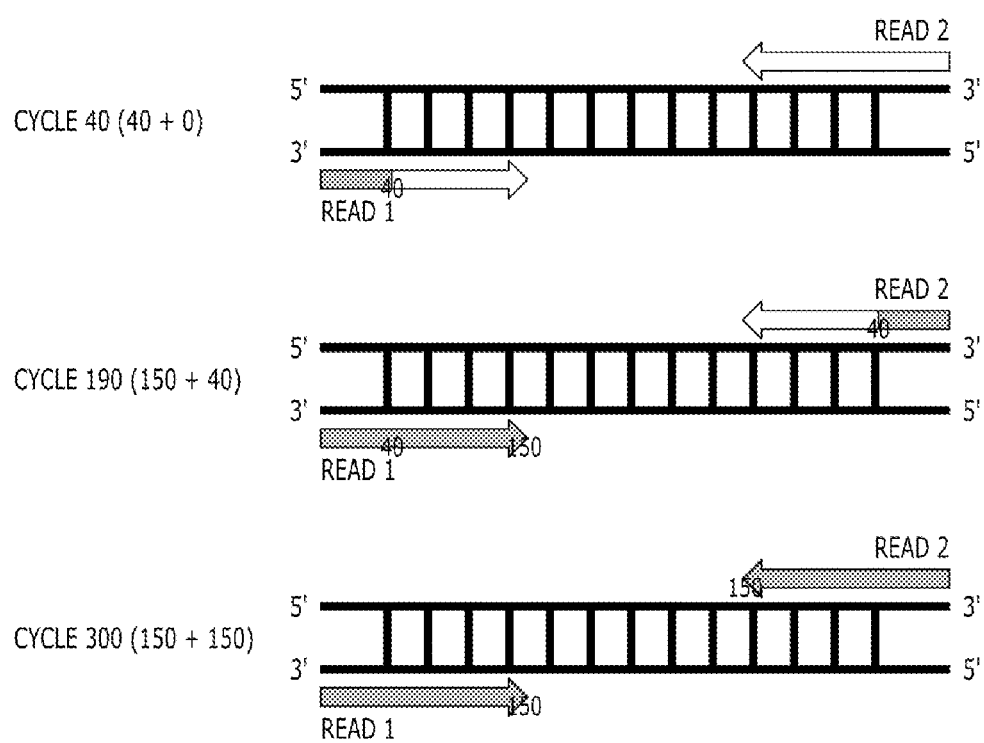
FIG. 3 is a diagram illustrating paired-end reads.

A method for analyzing sequences performed by one or more processors included in the information processing system 110 will be described in more detail with reference to FIG. 3 to FIG. 2 is a block diagram illustrating an internal configuration of the information processing system 110. The information processing system 110 may be a system for analyzing the whole genome sequencing result. The information processing system 110 may include a memory 210, a processor 220, a communication module 230, and an input and output interface 240. As illustrated in FIG. 2, the information processing system 110 may be configured to communicate information and/or data through a network by using the communication module 230.

The memory 210 may include any non-transitory computer-readable recording medium. The memory 210 may include a permanent mass storage device such as read only memory (ROM), disk drive, solid state drive (SSD), flash memory, and so on. In another example, a non-destructive mass storage device such as ROM, SSD, flash memory, disk drive, and so on may be included in the information processing system 110 as a separate permanent storage device that is distinct from the memory. In addition, the memory 210 may store an operating system and at least one program code (e.g., a code for analyzing sequences installed and driven in the information processing system 110). In FIG. 2, the memory 210 is illustrated as a single memory, but this is only for convenience of description, and the memory 210 may include a plurality of memories.

These software components may be loaded from a computer-readable recording medium separate from the memory 210. Such a separate computer-readable recording medium may include a recording medium directly connectable to the information processing system 110, and may include a computer-readable recording medium such as a floppy drive, a disk, a tape, a DVD/CD-ROM drive, a memory card, etc., for example. In another example, the software components may be loaded into the memory 210 through the communication module 230 rather than the computer-readable recording medium. For example, at least one program may be loaded into the memory 210 based on a computer program (e.g., a program or the like for analyzing sequences, etc.) installed by the files provided by the developers, or by a file distribution system that distributes an installation file of an application through the communication module 230.

The communication module 230 may provide a configuration or function for the user terminal and/or an external device and the information processing system 110 to communicate with each other through a network, and may provide a configuration or function for the information processing system 110 to communicate with an external system (e.g., a separate cloud system).

In addition, the input and output interface 240 of the information processing system 110 may be a means for interfacing with a device (not illustrated) for inputting or outputting, which may be connected to the information processing system 110 or included in the information processing system 110. For example, the input and output interface 240 may include at least one of a PCI express interface and an Ethernet interface. In FIG. 2, the input and output interface 240 is illustrated as a component configured separately from the processor 220, but aspects are not limited thereto, and the input and output interface 240 may be configured to be included in the processor 220. The information processing system 110 may include more components than those illustrated in FIG. 2.

The processor 220 may be configured to process the commands of the computer program by performing basic arithmetic, logic, and input and output operations. For example, the processor 220 may be configured to execute one or more instructions of the memory 210 to acquire a first marking code, which is generated by the sequencer 120 at a first time point that is earlier than a completion time point at which the marking codes of all cycles are generated by the sequencer 120, convert the first marking code into a first nucleotide identifier, align the first sequence data including the first nucleotide identifier based on the reference sequence data, identify a variant from the first sequence data, and generate a first report including the variant identified before the completion time point.

In FIG. 2, the processor 220 is illustrated as a single processor, but this is only for convenience of description, and the processor 220 may include a plurality of processors. If a plurality of processors are included, each processor included in an information processing system 110 may operate in parallel. For example, if the information processing system 110 includes a first processor, a second processor, and a third processor, the first processor may be configured to convert the first marking data acquired at the first time point into a first nucleotide identifier, the second processor may be configured to convert the second marking data acquired at a second time point into a second nucleotide identifier, and the third processor may be configured to align sequence data including the first nucleotide identifier and the second nucleotide identifier. In this case, the second time point may be later than the first time point, and the third time point may be later than the second time point.

FIG. 3 is a diagram illustrating paired-end reads. As illustrated in FIG. 3, a pair of reads may be output as a result of sequencing one DNA fragment. The sequencer 120 may identify one nucleotide in each DNA fragment for every cycle, and generate a marking code indicating the type of the identified nucleotide for each DNA fragment. The generated marking code may be recorded in the marking data. The number of marking codes and the number of marking data may correspond to the number of DNA fragments.

As illustrated in FIG. 3, the sequencer 120 may identify 150 nucleotides, for example from one end of one DNA fragment and record the result as a first read (read1), and if identification of 150 nucleotides is completed, the sequencer 120 may reverse the DNA fragment to identify 150 nucleotides from the opposite end and record the result as a second read (read2). The sequencer 120 may identify one nucleotide per cycle. As illustrated in FIG. 3, if 150 nucleotides are read from both ends of each DNA fragment, respectively, the sequencer 120 may perform a total of 300 cycles.

In some examples, adapters may be attached to both ends of the DNA fragment. The adapter may include a series of nucleotides for expressing an identifier that distinguishes the DNA fragment of the first test subject from the DNA fragment of the second test subject. In the following description of the present disclosure, the cycle required for reading the adapter is ignored. The report may be provided to the client several times. For example, a first report, or an initial report, may be generated and provided to the client at the time of the first early analysis, e.g., at the time when sequencing is completed up to cycle 40, a second report, or an interim report, may be generated and provided to the client at the time of the second early analysis, e.g., at the time when 190 cycles are completed, and a third report, or a final report, may be generated and provided to the client at the time of the final analysis, e.g., at the time when 300 cycles are completed. Each report generation cycle is merely an example, and the report generation cycle and/or the number of report generation times may be determined according to a setting by an administrator.

At the time when 40 cycles are completed (Cycle 40 in FIG. 3), the first report may be generated by the information processing system 110 and provided to the client. That is, before a total of 300 cycles are completed, the first marking data, which is partial marking data acquired during 40 cycles, may be converted into the first sequence data. As a result, the first sequence data may include 40 nucleotide identifiers. Next, the information processing system 110 may use the reference sequence data to align the first sequence data, identify a variant from the first sequence data, and generate a first report based on the identified variant.

At a time when 190 cycles (Cycle 190 in FIG. 3) are completed, a second report may be generated by the information processing system 110 and reported to the client. The second report may be a report generated by updating the first report. That is, before the completion of a total of 300 cycles, the second marking data acquired at the time when 190 cycles are completed may be converted into the second sequence data. In this case, the second marking data may be generated by adding 150 marking codes to the first marking data. The second sequence data converted from the second marking data may include the first sequence data. As a result, the second sequence data may include 190 nucleotide identifiers. In other words, 150 marking codes may be added to the first marking data to generate second marking data, and accordingly, the second sequence data may further include 150 nucleotide identifiers compared to the first sequence data. The information processing system 110 may use the reference sequence data to align the second sequence data, identify a variant from the second sequence data, and generate a second report based on the identified variant.

In addition, at a time when 300 cycles (Cycle 300 in FIG. 3) is completed, a third report may be generated by the information processing system 110 and reported to the client. The third report may be an update of the second report. That is, if a total of 300 cycles are performed to identify nucleotides for all DNA fragments and the sequencing operation by the sequencer 120 is completed, the entire marking data may be converted into the third sequence data. In this case, the third sequence data may include the second sequence data. That is, 110 marking codes may be added to the second marking data to generate the third marking data, and accordingly, the third sequence data may further include 110 nucleotide identifiers compared to the second sequence data. The information processing system 110 may align the third sequence data based on the reference sequence data, identify a variant from the third sequence data, and generate a third report based on the identified variant.

The accuracy of the variant calling may increase from the first report to the third report. That is, as more nucleotide identifiers are accumulated in the sequence data, the accuracy of variant calling may increase. Meanwhile, regarding the timing of the report being provided, the first report is the earliest. That is, since the first report can be generated when 40 cycles are completed, the lead time may be very shorter compared to the second report generated at cycle 190 and the third report generated at cycle 300.

According to the examples of the present disclosure, whether or not the variants recorded in each report occur may slightly vary in sensitivity, but there is rarely a case in which a variant identified in an earlier report is denied in a later report. In other words, the testing process of the present disclosure shows a tendency that the number of unfound variants are decreased from the analysis time point at cycle 40 towards the analysis time point at cycle 190, and from the analysis time point at cycle 190 towards the analysis time point at cycle 300. There is rarely a case that the presence or absence of a variant determined in the early analysis is determined differently (i.e., false positive or false negative) in the subsequent analysis.

Accordingly, if the first report is generated based on the data acquired at cycle 40 and provided to the client at an early stage, the client can quickly prepare an appropriate treatment strategy based on the information on the variant occurring in the test subject's body without waiting for the final report to be provided. In addition, through additional reports subsequently provided at 190 cycle and 300 cycle, the client can reevaluate the treatment strategy he or she prepared previously. According to some examples, the estimated accuracy of variant calling at that time point may be indicated in the first report so that the client receiving the first report can determine whether or not to use this early report, i.e., the first report, for treatment purposes based on the estimated accuracy. If it is determined that the estimated accuracy of the variant calling in the first report is below a certain threshold, the client may not determine a treatment strategy at the time the first report is provided, but may determine the treatment strategy after receiving the second or third report.

In the present disclosure, the cycle 40, the cycle 190 (150+40), and the cycle 300 (150+150) have been described for convenience of description, but aspects are not limited thereto. For example, the cycle associated with the first report may be set to another cycle (e.g., one of cycles 35 to 60) when early detection of point mutations is easy. Meanwhile, the cycles of up to cycle are exemplified above, because if the length of the sequence output as a result of the sequencing exceeds a specific threshold length, the rate or probability of alignment (mapping) based on the reference sequence data no longer rapidly increases, but it is of course possible that the cycles beyond the cycle 60 may be set. As another example, the cycle associated with the second report may be set to a cycle when the early detection of structural variants is easy (e.g., any one in the range of 190–a to 190+b cycles or less, where a and b are natural numbers). In addition, although it is illustrated that one read has a length of 150, aspects are not limited thereto, and reads having different lengths may be generated depending on a sequencer.

The first and second early analysis time points may be replaced with time points other than cycle 40 and cycle 190. For example, the time of early analysis may depend on what a target value of a ratio, which indicates, among all reads to be processed, how many reads are uniquely mapped to any specific position on the reference sequence, respectively, is selected. For example, if it is desired that the ratio (that is, alignment ratio) of reads to be uniquely mapped to a specific position on the reference sequence among all reads to be processed at the time of the first and second early analysis is 97.5% or more, cycle 35 or later may be selected as the first early analysis time point and cycle 185 or later may be selected as the second early analysis time point. As another example, if it is desired that the ratio of uniquely mapped reads to specific positions on the reference sequence at the time of the first and second early analysis is 98.8% or more, cycle 40 or later may selected as the first early analysis time point and cycle 190 or later may be selected as the second early analysis time point.

In this case, the alignment ratio may be a ratio of reads uniquely aligned with the sub-region to all the reads included in the sequence data. For example, if the total number of sequence data is 10,000 and the number of reads uniquely aligned with the sub-regions is 9,800, the alignment ratio may be 98%. If target alignment ratio is set to 97.5% and the actual alignment ratio at a certain cycle is 98%, the alignment of the sequence data in that cycle may be determined to be successful. As another example, if the target alignment ratio is set to 98.8% and the actual alignment ratio is 98%, the alignment of the sequence data in that cycle may be determined to have failed.

Figure 4:
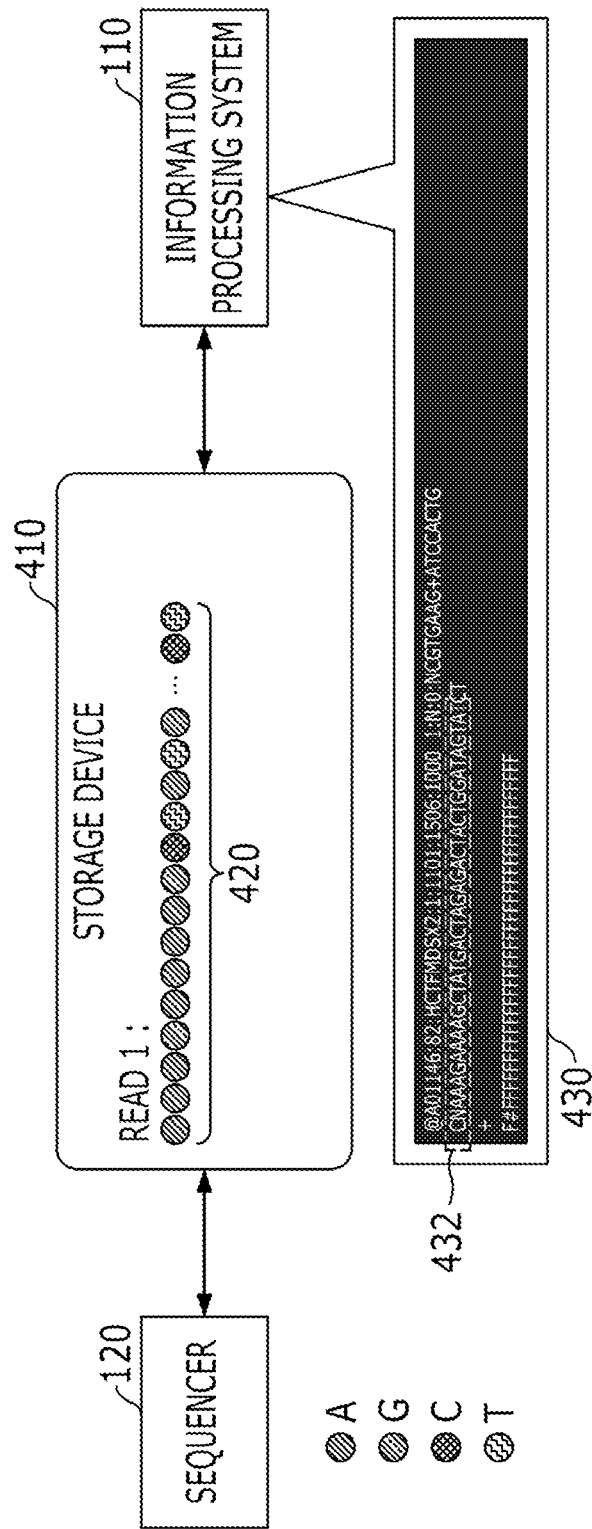
FIG. 4 is a diagram illustrating first sequence data converted from marking data generated at cycle 40.
Figure 5:
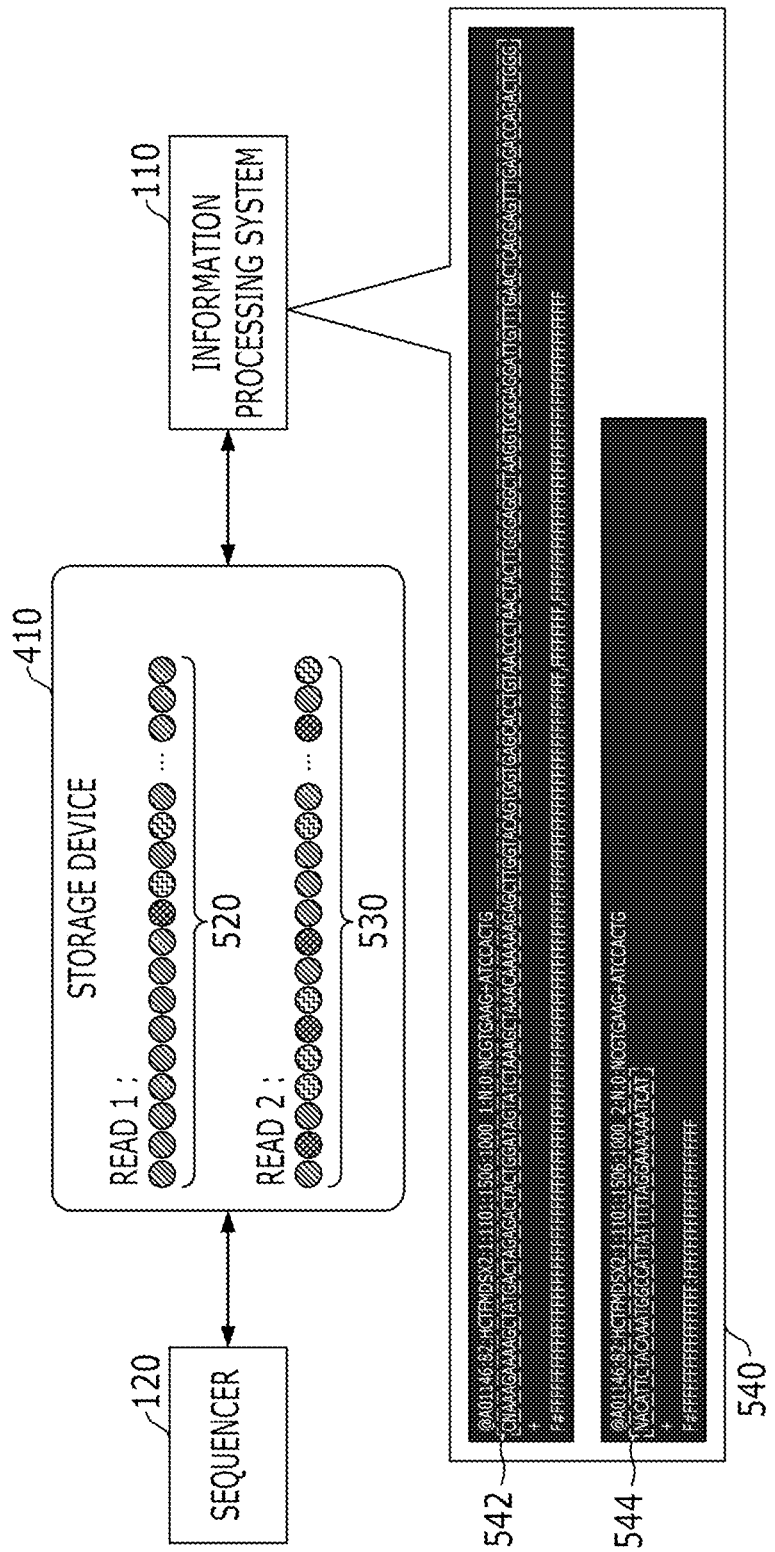
FIG. 5 is a diagram illustrating second sequence data converted from marking data generated at cycle 190.
Figure 6:
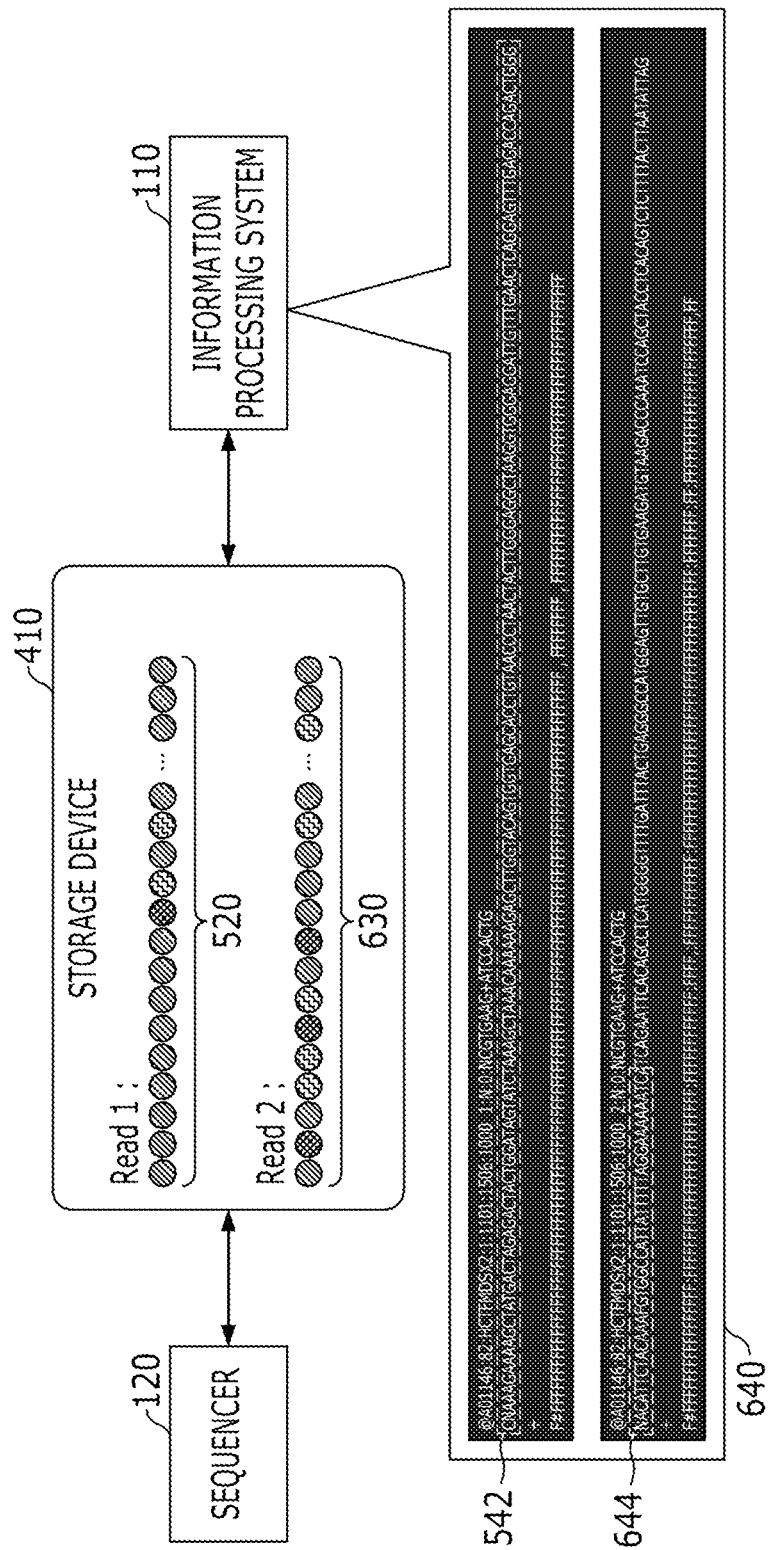
FIG. 6 is a diagram illustrating second sequence data converted from marking data generated at cycle 300.

FIG. 4 is a diagram illustrating first sequence data 432 converted from marking data 420 generated at cycle 40. Referring to FIG. 4, with the start of sequencing operation, the sequencer 120 may generate the marking data and store the same in a storage device 410. For example, the sequencer 120 may sequentially identify the marking codes of all DNA fragments one by one for each cycle, and record the identified marking codes in the marking data. The marking data of the storage device 410 may include a marking code separated for each DNA fragment, and the marking data may be updated for every cycle. If the marking code is recorded in the marking data for each cycle as described above, the first marking data 420 having 40 marking codes may be stored in the storage device 410 at the time when cycle 40 is completed. For example, using the sequencer of the NovaSeq 6000 equipment of Illumina, Inc., the first marking data 420 may be output in the form of BCL file. For convenience of explanation, FIGS. 4 to 6 illustrate that sequence data is generated or updated with respect to the marking code read from one DNA fragment.

If the first marking data 420 is stored in the storage device 410, the information processing system 110 may acquire the first marking data 420 stored in the storage device 410. The information processing system 110 may convert each marking code included in the acquired first marking data 420 into a nucleotide identifier to generate the first sequence data 432 including a plurality of nucleotide identifiers. For example, using the sequencer of the NovaSeq 6000 equipment of Illumina, Inc., the sequence data 432 may be output in the form of FASTQ file.

FIG. 4 illustrates that the marking data 420 including 40 marking codes for the 40 cycles is included in the storage device 410. In this case, the marking codes may be detected and identified optically, and among various properties of the marking code, fluorescent colors may be utilized. For example, a first fluorescent color may represent adenine, a second fluorescent color may represent cytosine, a third fluorescent color may represent guanine, and a fourth fluorescent color may represent thymine. The first to fourth fluorescent colors may be different from each other.

The information processing system 110 may access the storage device 410 and convert the marking data 420 into the first sequence data 432. As illustrated in FIG. 4, the information processing system 110 may convert the marking data 420 including 40 marking codes at cycle 40 into the first sequence data 432 including 40 nucleotide identifiers.

FIG. 4 illustrates a sequence file (e.g., FASTQ file) 430 including the first sequence data 432. The sequence file may include a header line, a line of sequence data (i.e., sequence identifiers) and a line indicating an accuracy of the sequence data. The header may be recorded in the first line of the sequence file, and may include identifiers of the read, the sequencer 120, and etc.

The first sequence data 432 may include a plurality of nucleotide identifiers (see line 2). FIG. 4 illustrates that there are 40 nucleotide identifiers included. Nucleotide identifiers may include characters "A", "T", "G", and "C." Character "N" may indicate that a base could not be read.

For the degree of accuracy for the sequence identifier (see line 4), a predefined letter may be used. If the marking code is correctly converted into the nucleotide identifier, "F" may be recorded, and if the marking code cannot be read, "#" may be recorded.

In addition, the information processing system 110 may align the first sequence data 432 at a specific position on the reference sequence and compare the aligned first sequence data 432 with the reference sequence data to identify a variant occurring in the first sequence data 432. At this time, the information processing system 110 may compare the first sequence data 432 with the reference sequence data to identify a position where each of reads included in the first sequence data 432 should be aligned and align the first sequence data 432 to the identified position. That is, the information processing system 110 may align (map) the first sequence data 432 using the reference sequence data as a kind of map data. The alignment of the sequence data, which will be described below, may be understood as the alignment (mapping) of each of reads included in the sequence data with the sub-region included in the entire reference region.

If an occurrence of a variant is determined, the information processing system 110 may generate a first report including detailed information on the corresponding variant (e.g., variant occurrence position), information on accuracy of variant occurrence determination, etc. and provide the generated first report to the client. The information processing system 110 may compare the reference sequence data with the aligned first sequence data to identify one or more nucleotide identifiers and positions differing from the reference sequence data, and identify a variant for the first sequence data based on the identified positions and one or more nucleotide identifiers.

A first report (that is, an early report) may be provided to a client at a time point much earlier than the time point at which all cycles (e.g., 300 cycles) proceed, and in an emergency situation, the client may refer to the first report to quickly determine how to treat the patient.

In some examples, the information processing system 110 may access the storage device 410 as soon as the new marking code is recorded in the marking data, updating the marking data, and convert the new marking code into a nucleotide identifier in real time. The converted nucleotide identifier may be additionally recorded in the already generated sequence data, thus updating the sequence data. Accordingly, the marking code may be converted into a nucleotide identifier in real time.

In this case, by the real-time conversion, it may mean that the new marking code is converted into a nucleotide identifier in response to the new marking code being stored in the storage device 410. For example, the information processing system 110 may monitor whether or not the new marking code is stored in the storage device 410, and if the new marking code is stored, the information processing system 110 may convert the new marking code into a nucleotide identifier in real time.

Referring to FIG. 4 as an example, as soon as the new marking code is additionally recorded in the marking data, the information processing system 110 may immediately convert the new marking code into a nucleotide identifier. In addition, the information processing system 110 may additionally record the converted nucleotide identifier in the sequence data to update the sequence data.

If a threshold number (e.g., 40) of nucleotide identifiers included in the sequence data is accumulated, the information processing system 110 may perform the alignment with respect to the sequence data. That is, the smaller the number of nucleotide identifiers included in the sequence data, the higher the likelihood that these are aligned at two or more positions on the reference sequence. Accordingly, the information processing system 110 may wait for the nucleotide identifiers to be accumulated up to a predetermined number or more, and align the sequence data in response to the predetermined number or more of the nucleotide identifiers being accumulated in the sequence data.

Meanwhile, a situation may occur in which sequence data alignment is still impossible despite the accumulation of the predetermined number or more of the nucleotide identifiers in the sequence data. For example, a code related to omission/deletion, inability to read, etc. of a nucleotide identifier may be recorded in the sequence data. In this case, the alignment with respect to the sequence data may not be possible.

In addition, if it is not possible to uniquely specify, from the entire reference region, a sub-region where a read included in the sequence data should be positioned, alignment of the read may fail. For example, the entire reference region associated with the reference sequence data may include a plurality of sub-regions. If it is determined that there are a plurality of sub-regions matching the nucleotide identifiers included in the read, it may not be possible to determine which sub-region is to be specified for the read among the plurality of sub-regions. For example, if a read coincides with both the first and second sub-regions in a certain cycle, it may be ambiguous which of the first sub-region and the second sub-region is to be aligned with the read.

The information processing system may calculate a ratio of reads uniquely aligned to a sub-region to the respective reads included in the sequence data, and determine whether or not the calculated alignment ratio is equal to or greater than a target alignment ratio. For example, if the total number of reads included in the entire sequence data is 10000, and the number of reads uniquely mapped to the sub-region is 9800, the information processing system may calculate that the alignment ratio is 98%. If the alignment ratio is equal to or greater than the target alignment ratio, the information processing system may determine that alignment with respect to the sequence data is successful. Meanwhile, if the alignment ratio is less than the target alignment ratio, the information processing system may determine that alignment with respect to the sequence data fails.

In preparation for such an aligning failure situation, the information processing system 110 may defer the alignment of the sequence data in the current cycle if the predetermined or more of the nucleotide identifiers are accumulated in the sequence data but the alignment of the sequence data fails. The information processing system 110 may retry the alignment with respect to the sequence data if a preset number of additional nucleotide identifiers are further included in the sequence data.

FIG. 5 is a diagram illustrating second sequence data 542 and 544 converted from marking data 520 and 530 generated at cycle 190. As illustrated in FIG. 5, at cycle 190, the marking data 520 for the first read (Read 1) and the marking data 530 for the second read (Read 2) generated in the sequencer 120 may be stored in the storage device 410. In this case, the marking data 520 for the first read (Read 1) may include 150 marking codes, and the marking data 530 for the second read (Read 2) may include 40 marking codes. For example, using the sequencer of NovaSeq 6000 equipment of Illumina, Inc., the marking data 520 for the first read (Read 1) and the marking data 530 for the second read (Read 2) may be output in the form of BCL file.

The information processing system 110 may access the storage device 410 and convert the marking data 520 and 530 into the second sequence data 542 and 544. As illustrated in FIG. the information processing system 110 may convert the marking data 520 and 530 including 190 marking codes accumulated during 190 cycles into the second sequence data 542 and 544 including 190 nucleotide identifiers. FIG. 5 illustrates that the second sequence data includes the sequence data 542 for the first read and sequence data 544 for the second read. In FIG. 5, a sequence file 540 including the second sequence data 542 and 544, a header, etc. is illustrated. For example, using the sequencer of the NovaSeq 6000 equipment of Illumina, Inc., the sequence file 540 may be output in the form of FASTQ file.

The information processing system 110 may align the second sequence data 542 and 544 to a specific position on the reference sequence. In addition, the information processing system 110 may compare the aligned second sequence data 542 and 544 with the reference sequence data to determine the occurrence of a variant in the second sequence data. If it is determined that a variant occurred, the information processing system 110 may generate a second report including detailed information on the corresponding variant (e.g., variant occurrence position), information on accuracy of variant occurrence determination, etc. and provide the generated second report to the client. The second report may be an update of the first report.

Accordingly, the second report (that is, the interim report) may be provided to the client at a time earlier than the time point at which all cycles (e.g., 300 cycles) proceed, and the client may compare the first and second reports to determine whether or not to continue the treatment method that was determined with the first report provided.

According to some examples, if the new marking code is additionally recorded in the storage device 410, the information processing system 110 may convert the new marking code into a nucleotide identifier in real time. If the alignment of the sequence data is completed, the information processing system 110 may arrange the subsequently converted nucleotide identifier adjacent to a nucleotide identifier that is previously converted and aligned. For example, if the first sequence data generated at cycle 40 is in an aligned state, the nucleotide identifier converted at cycle 41 may be positioned adjacent to the nucleotide identifier positioned at the very end of the first sequence data. As another example, a nucleotide identifier converted at cycle 42 may be positioned adjacent to the nucleotide identifier converted at cycle 41. Accordingly, the conversion and alignment of the nucleotide identifier may be performed simultaneously.

FIG. 6 is a diagram illustrating second sequence data 542 and 644 converted from marking data 520 and 630 generated at cycle 300. As illustrated in FIG. 6, at cycle 300, the marking data 520 for the first read (Read 1) and the marking data 630 for the second read (Read 2) generated in the sequencer 120 may be stored in the storage device 410. In this case, cycle 300 may be a cycle in which the sequencing operation is completed. In addition, the marking data 520 for the first read (Read 1) may include 150 marking codes, and the marking data 630 for the second read (Read 2) may include 150 marking codes. For example, using the sequencer of NovaSeq 6000 equipment of Illumina, Inc., the marking data 520 for the first read (Read 1) and the marking data 630 for the second read (Read 2) may be output in the form of BCL file.

The information processing system 110 may access the storage device 410 and convert the marking data 520 and 630 into the third sequence data 542 and 644. As illustrated in FIG. 6, the information processing system 110 may convert the marking data 520 and 630 including 300 marking codes accumulated during 300 cycles into the third sequence data 542 and 644 including 300 nucleotide identifiers. FIG. 6 illustrates a sequence file 640 related to the third sequence data including the sequence data 542 for the first read and the sequence data 644 for the second read. For example, using the sequencer of the NovaSeq 6000 equipment of Illumina, Inc., the sequence file 640 may be output in the form of FASTQ file.

The information processing system 110 may align the third sequence data 542 and 644 based on the reference sequence data. In addition, the information processing system 110 may compare the aligned the third sequence data 542 and 644 with the reference sequence data to determine the occurrence of a variant in the third sequence data 542 and 644. If it is determined that a variant occurred, the information processing system 110 may generate a third report including detailed information on the corresponding variant (e.g., variant occurrence position), information on accuracy of variant occurrence determination, etc. and provide the generated third report to the client. The third report may be an update of the second report.

Accordingly, if all cycles (e.g., 300 cycles) are completed, a third report (that is, final report) may be provided to the client, and the client may compare the third report with the first report and/or the second report to determine whether or not to continue the treatment method that was determined with the first or second report provided.

FIG. 7 is a diagram illustrating a result of variant occurrence determination included in the first report and the second report. FIG. 7A illustrates data included in the first report, showing variants identified based on the first sequence data accumulated over 40 cycles. That is, FIG. 7A illustrates that the mutation related to the gene "EGFR" is identified at the time of early analysis of cycle 40, and that the variant is not identified with respect to the gene "KRAS". In addition, FIG. 7A illustrates that the false positive rate of the gene "EGFR" is 5% and the false negative rate of the gene "KRAS" is 40%.

FIG. 7B illustrates data included in the second report, showing variants identified based on the second sequence data accumulated over 190 cycles. That is, in FIG. 7B, the false positive rate for the mutations related to the gene "EGFR" is recorded, and also the false negative rate for the mutations related to the gene "KRAS" is recorded.

By comparing the first report related to FIG. 7A and the second report related to FIG. 7B, it can be seen that the false positive rate of "EGFR" is decreased, and thus the accuracy of variant positive of the gene "EGFR" is gradually increased. In addition, it can be seen that the false negative rate of "KRAS" is increased, and accordingly, the accuracy of the variant negative of the gene "KRAS" is gradually increased.

Figure 8:
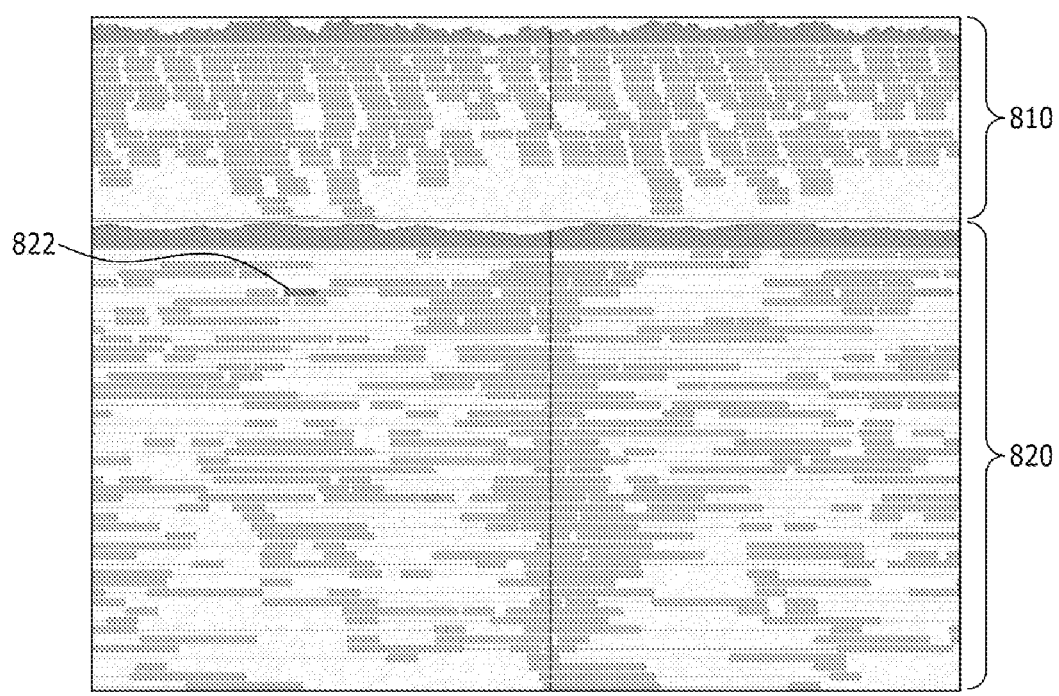
FIG. 8 is an exemplary diagram showing a comparison between a variant identified at cycle 40 and a variant identified at cycle 190.

FIG. 8 is an exemplary diagram showing a comparison between a variant identified at cycle 40 and a variant identified at cycle 190. In a first region 810 of FIG. 8, the first sequence data may be displayed, with the point mutations identified from the first sequence data being displayed in the form of a dotted line in a vertical direction. In this case, the first sequence data may be the sequence data that is converted from the marking data acquired during 40 cycles and includes a plurality of reads.

In addition, in a second region 820 of FIG. 8, the second sequence data may be displayed, with the point mutations identified from the second sequence data being displayed in the form of a dotted line in a vertical direction. In this case, the structural variants may be displayed in a specific color 822. In this case, the second sequence data may be the sequence data that is converted from the marking data acquired during 190 cycles and includes a plurality of reads.

By comparing the first region 810 and the second region 820, it can be seen that the point mutations identified in the first sequence data and the second sequence data are almost identical. This implies that it is possible to identify most of the point mutations by the analysis of the marking data acquired during 40 cycles without having to wait for all sequencing operations to be completed by the sequencer 120. Accordingly, the variant determination of the first report provided at the time when 40 cycles are completed can be reliably referenced. Meanwhile, it can be observed that the structural variants displayed in the color 822 in FIG. 8 are not identified in the first sequence data whereas they are identified in the second sequence data.

FIG. 9 is an exemplary chart comparing each analysis time point in terms of expected sensitivity and the sequencing amount. In FIG. 9, the unit "X" of the expected reach may indicate the average number of times the entire region of the human genome including $3.3 \times 10^9$ nucleotides is read. For example, "10X" may mean that the human genome including $3.3 \times 10^9$ nucleotides is read 10 times on average, and a total of $33 \times 10^9$ base pairs of sequences are acquired. That is, the unit of expected reach may be related to the time it takes to reach the target sequencing amount.

Referring to FIG. 9, referring to the analysis result of the sequence data at cycle 40, it can be seen that the analysis result at cycle 40 can be obtained the earliest because the target sequencing amount and the expected reach are the smallest, but the analysis result at cycle 40 has the lowest point mutation detection sensitivity and detection sensitivity at 80% of the tumor cell ratio. On the other hand, referring to the analysis result of the sequence data at cycle 300, it can be seen that analysis result at cycle 300 takes the longest time to be obtained because the target sequencing amount and the expected reach are the largest, but analysis result at cycle 300 has the highest mutation detection sensitivity and detection sensitivity at 80% of the tumor cell ratio.

As illustrated in FIG. 9, by comparing the analysis result for the sequence data at cycle 40 and the analysis result at another cycle, it can be seen that there is a difference of about 6% point in the point mutation detection sensitivity, and a difference of about 7% point in the detection sensitivity at 80% of the tumor cell ratio. This difference does not impair the degree of detection in accuracy and it can be considered that the first report generated based on the sequence data converted at cycle 40 can be used reliably. In addition, referring to the analysis result for the sequence data at cycle 190 (150+40), it can be seen that the point mutation detection sensitivity is substantially similar to the analysis result of cycle 300, and the detection sensitivity at 80% of the tumor cell ratio is only slightly different from the analysis result of cycle 300.

Accordingly, the first report can be used reliably for the detection of point mutations, and more reliable mutation information can be additionally provided to the client through the second report provided as an interim report. The client in an emergency situation can establish a treatment plan for the patient in advance by referring to the first report and/or the second report, without waiting for the final report.

Meanwhile, the information processing system may be configured to include a plurality of computing nodes, in which case the respective computing nodes may operate in parallel.

Figure 10:
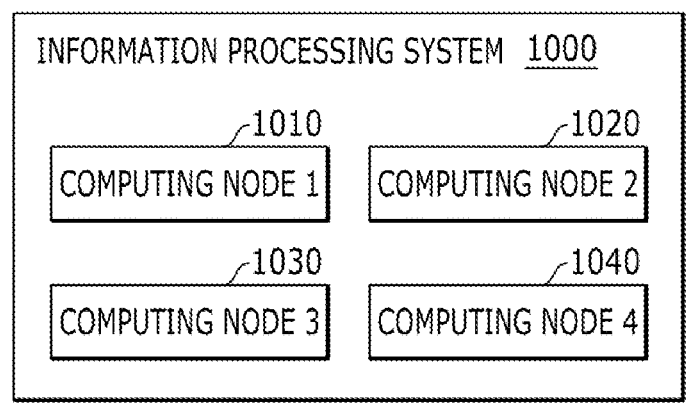
FIG. 10 is a diagram illustrating an information system including a plurality of computing nodes.

FIG. 10 is a diagram illustrating an information system 1000 including a plurality of computing nodes 1010 to 1040. As illustrated in FIG. 10, the information processing system 1000 may include the plurality of computing nodes 1010 to 1040, and the respective computing nodes 1010 to 1040 may operate in parallel. In this case, the respective computing nodes 1010 to 1040 may be configured to take charge of a specific function. For example, an computing node 1 (1010) may convert the marking data acquired in odd-numbered cycles into nucleotide identifiers, and an computing node 2 (1020) may convert the marking data acquired in even-numbered cycles into nucleotide identifiers. In addition, an computing node 3 (1030) may integrate the converted nucleotide identifiers to generate sequence data and align the sequence data. A computing node 4 (1040) may identify a variant from the sequence data and generate a report based on the identified variant.

The respective computing nodes 1010 to 1040 may be related to one or more processors. For example, the information processing system 1000 may include a plurality of processors, and the computing node 1 (1010) may be related to a first processor, the computing node 2 (1020) may be related to a second processor, the computing node 3 (1030) may be related to a third processor, and the computing node 4 (1040) may be related to the fourth processor. In this case, the computing node 1 (1010) related to the first processor may convert an odd-numbered first marking code acquired from the storage device at a first time point into a first nucleotide identifier, the computing node 2 (1020) related to the second processor may convert an even-numbered second marking code obtained from the storage device at the second time point into a second nucleotide identifier, and the computing node 3 (1030) related to the third processor may align sequence data including the first nucleotide identifier and the second nucleotide identifier.

Figure 11:
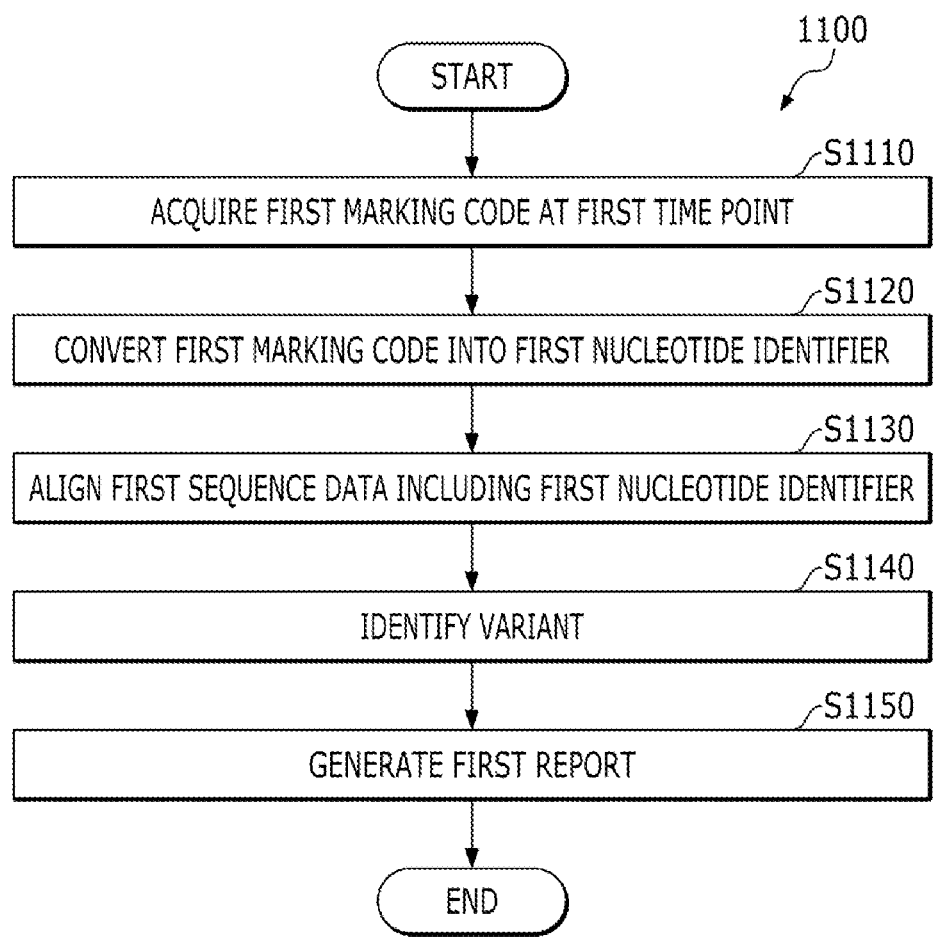
FIG. 11 is a flowchart illustrating a method for analyzing sequences at a first time point.
Figure 12:
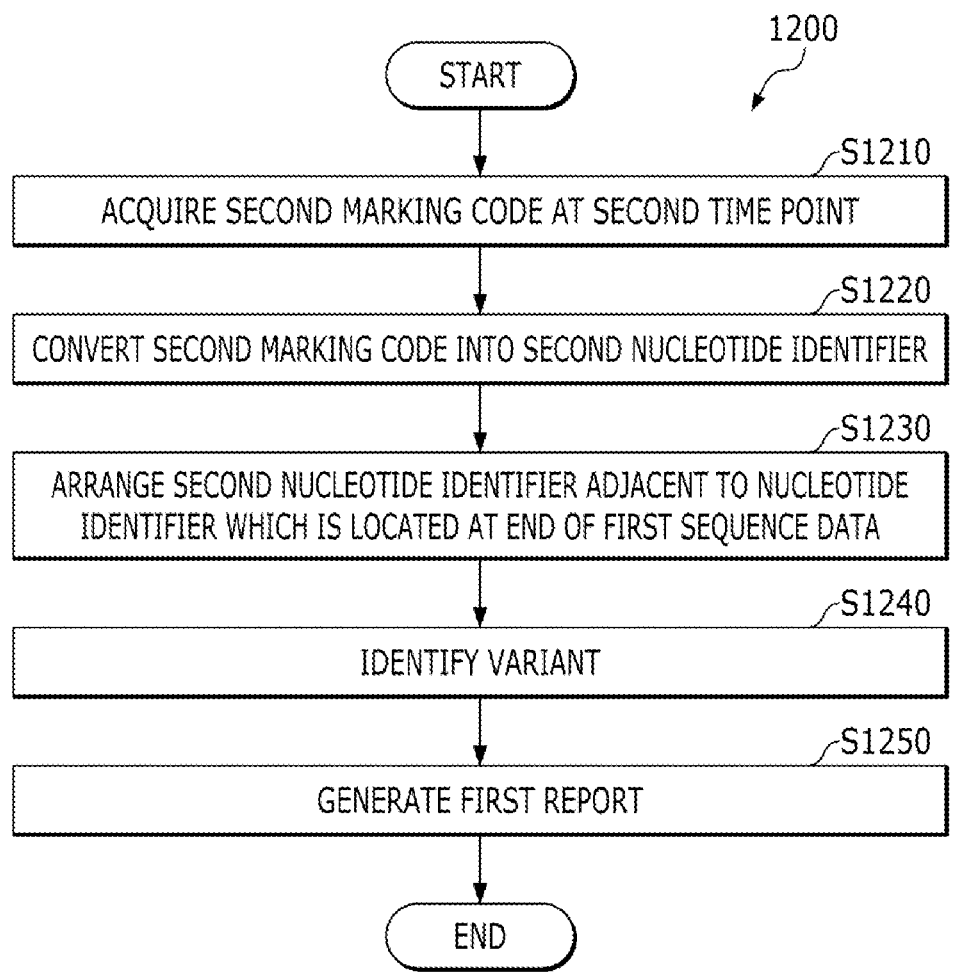
FIG. 12 is a flowchart illustrating a method for analyzing sequences at a second time point.
Figure 13:
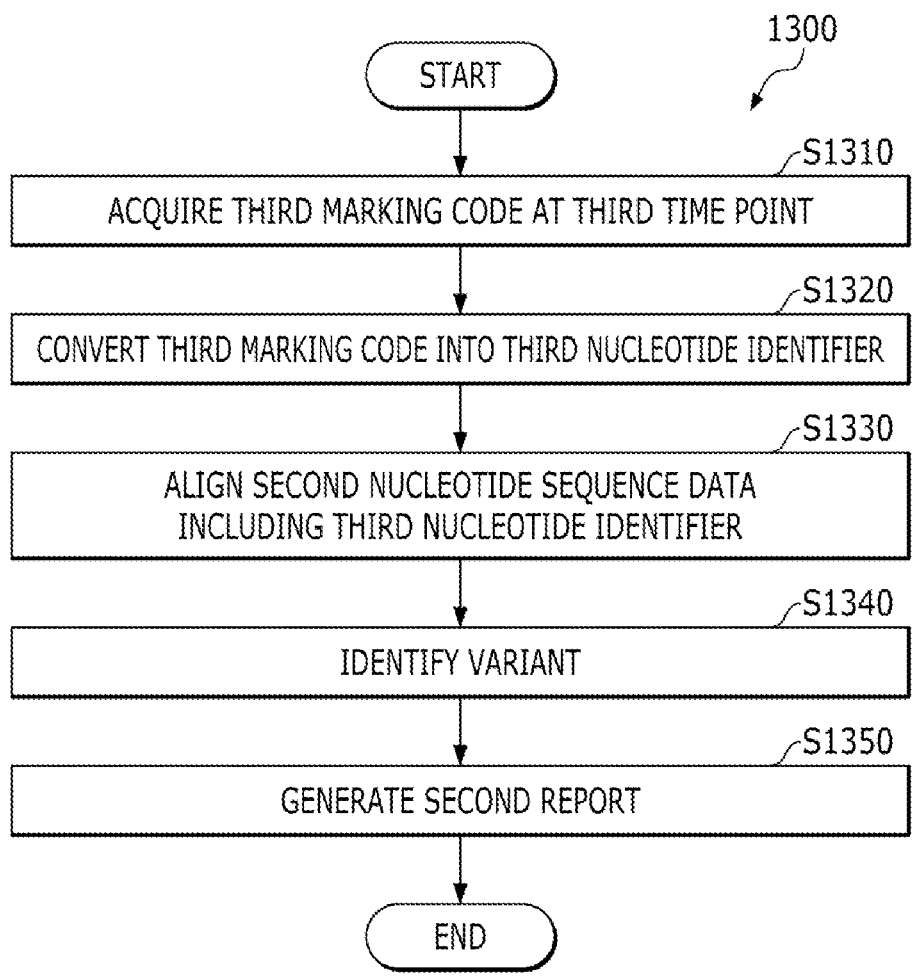
FIG. 13 is a flowchart illustrating a method for analyzing sequences at a third time point.

FIG. 11 is a flowchart illustrating a method 1100 for analyzing sequences at the first time point. The method illustrated in FIGS. 11 to 13 is merely examples of achieving the object of the present disclosure, and it goes without saying that some steps may be added or deleted as necessary. In addition, the method illustrated in FIGS. 11 to 13 may be performed by one or more processors included in the information processing system. For convenience of description, it will be described that each step illustrated in FIGS. 11 to 13 is performed by a processor included in the information processing system illustrated in FIG. 1.

The processor may acquire the first marking code generated by the sequencer at the first time point, at S1110. In this case, the first time point may be before the completion time point at which all the marking codes are generated by the sequencer. For example, the first time point is a time point at which the partially read sequence data of the second read is sufficient to be aligned with reference sequence data. In response to the first marking code being stored in the storage device, the processor may convert the first marking code into the first nucleotide identifier in real time.

The processor may convert the first marking code into the first nucleotide identifier, at S1120. The first marking code may be an optically read code or image data, in which case the processor may convert the first marking code into a first nucleotide identifier based on attributes of the first marking code, such as a color or the like.

The processor may align the first sequence data including the first nucleotide identifier, at S1130. If the number of nucleotide identifiers included in the first sequence data reaches a threshold number, the processor may align the first sequence data based on the reference sequence data. That is, if a predetermined number or more of nucleotide identifiers are accumulated in the first sequence data, the processor may compare the first sequence data with the reference sequence data to identify a region in which the first sequence data is positioned, and align the first sequence data to the identified region. The processor may map the read included in the first sequence data to the sub-region included in the entire reference region to align the first sequence data.

In this case, the threshold number serving as a criterion for the data alignment may be determined based on at least one of the degree of emergency for the report or the amount of DNA of a test subject input to the sequencer. For example, in an emergency situation in which a report must be reported quickly, or if the amount of DNA of a test subject of interest input to the sequencer is relatively large, the threshold number may be determined to be a relatively small number. As another example, if the time when the report to be reported to the sequencer is not urgent or the amount of DNA of the test subject of interest among the total amount of DNA input to the sequencer is relatively small, the threshold number may be determined to be a relatively large number.

Additionally or alternatively, the threshold number may be determined in consideration of a sequencing unit cost. For example, if the sequencing unit cost is set high, the threshold number may be determined to be a relatively small number, and if the sequencing unit cost is set low, the threshold number may be determined to be a relatively large number.

Meanwhile, despite the first sequence data reaching the threshold number, alignment of the first sequence data may fail. For example, in the course of a marking operation of the sequencer and/or a conversion operation of the information processing system, unintentional situations, such as insertion of unintended nucleotide identifier into the first sequence data, or deletion of some nucleotide identifiers, etc. may occur. If such an unintentional situation occurs, a region that the first sequence data should be positioned may not be accurately identified, resulting in a failure of the alignment of the first sequence data.

The processor may calculate a ratio of reads uniquely aligned to a sub-region to the respective reads included in the sequence data, and determine whether or not the calculated alignment ratio is equal to or greater than a target alignment ratio. If the calculated alignment ratio is less than the target alignment ratio, the processor may determine that alignment with respect to the first sequence data fails.

In preparation for such an alignment failure situation, the processor may temporarily defer the alignment of the first sequence data if the alignment of the first sequence data fails. If the first sequence data further includes a preset number of additional nucleotide identifiers, the processor may align the first sequence data again. That is, the marking codes additionally generated by the sequencer may be converted into nucleotide identifiers, and the converted nucleotide identifiers may be further included in the first sequence data up to a preset number to update the first sequence data. In this case, the processor may perform the alignment with respect to the updated first sequence data again.

If the alignment of the first sequence data is completed, the processor may compare the reference sequence data with the first sequence data to identify the occurrence of a variant in the first sequence data, at S1140. If an occurrence of a variant is identified, the processor may identify a position in the first sequence data where the variant occurred and a gene corresponding thereto.

The processor may generate a first report (e.g., an initial report) including the identified variant, and provide the generated first report to the client, at S1150. In this case, the processor may send the first report to the client's e-mail or transmit to the client's terminal. The processor may include a false negative rate and/or a false positive rate for the variant in the first report. In this case, the processor may use at least one of an algorithm or a machine learning model for calculating the false negative rate and/or the false positive rate to calculate the false negative rate or the false positive rate for the variant.

FIG. 12 is a flowchart illustrating a method 1200 for analyzing sequences at a second time point. The method according to FIG. 12 may be performed after the method according to FIG. 11. That is, the second time point in FIG. 12 may be after the first time point in FIG. 11.

The processor may acquire the second marking code generated by the sequencer at the second time point, at S1210. In this case, the second time point may be before the completion time point at which all the marking codes are generated by the sequencer. In response to the second marking code being stored in the storage device, the processor may convert the second marking code into the second nucleotide identifier in real time.

The processor may convert the second marking code into the second nucleotide identifier, at S1220.

The processor may arrange the second nucleotide identifier adjacent to the nucleotide identifier which is positioned at the end of the already aligned first sequence data, at S1230. That is, in a situation in which the first sequence data is aligned and the sequencing operation for the read by the sequencer is not completed, if the additional second nucleotide identifier is converted, the processor may include the second nucleotide identifier in the already aligned first sequence data, while arranging the second nucleotide identifier such that the second nucleotide identifier is adjacent to the nucleotide identifier positioned at the end of the first sequence data. For example, after the first sequence data including the 40 nucleotide identifiers at cycle 40 is aligned, if the 41st marking code acquired at cycle 41 is converted into the 41st nucleotide identifier, the processor may arrange the 41st nucleotide identifier to be adjacent to the 40th nucleotide identifier.

As described above, if the first sequence data is already aligned, the additionally converted second nucleotide identifier may be arranged adjacent to the nucleotide identifier at the end of the already aligned first sequence data. In this case, the second nucleotide identifier may be included in the first sequence data, and accordingly, the first sequence data may be updated. According to this example, the conversion to the nucleotide identifier and the alignment can be performed at the same time, and thus the overall operation speed can be improved.

If the arrangement of the second nucleotide identifier is completed, the process may compare the first sequence data including the second nucleotide identifier with the reference sequence data to determine whether or not a variant is identified, at S1240. In this case, the processor may identify a new variant (e.g., a structural variant) from the first sequence data additionally including the second nucleotide identifier. If it is determined that the variant occurred, the processor may identify a position in the first sequence data and a gene where the variant occurred.

The processor may update the first report (e.g., the initial report) based on the identified variant, at S1250. The processor may determine whether or not additional reporting is necessary based on the updated first report, and if it is determined that additional reporting is necessary, the processor may report the updated first report to the client. If a new variant is additionally recorded in the first report, the processor may determine that additional reporting is necessary.

Meanwhile, in some examples, if the second marking code is acquired at the second time point, the processor may convert the marking data including the plurality of marking codes accumulated from the analysis start time to the second time point into sequence data. That is, instead of selecting only the second marking code at the second time point and converting it into a second nucleotide identifier, the processor may convert the marking data including the second marking code accumulated from the analysis start time to the second time point into the sequence data. In this case, all the marking codes accumulated at the second time point and included in the marking data may be converted into nucleotide identifiers. The processor may align the converted sequence data and identify a variant from the aligned sequence data.

FIG. 13 is a flowchart illustrating a method 1300 for analyzing sequences at the third time point. The method according to FIG. 13 may be performed after the method according to FIG. 11 and/or FIG. 12. That is, the third time point in FIG. 13 may be after the first time point in FIG. 11 and/or the second time point in FIG. 12.

The processor may acquire the third marking code generated by the sequencer at the third time point, at S1310. In this case, the third time point may be before the completion time point at which all the marking codes are generated by the sequencer. For example, the third time point may be a time point at which cycle 190 is completed. In response to the third marking code being stored in the storage device, the processor may convert the third marking code into the third nucleotide identifier in real time.

The processor may convert the third marking code into the third nucleotide identifier, at S1320.

The processor may align the second sequence data including the third nucleotide identifier, at S1130. If the second sequence data is already aligned, as described above, the processor may arrange the third nucleotide identifier adjacent to the nucleotide identifier which is positioned at the end of the aligned second sequence data. The second sequence data may include the first sequence data described with reference to FIG. 11. In this case, the first sequence data may be acquired based on the reading, by the sequencer, of a predetermined number of nucleotides from one end of the DNA fragment, and the second sequence data may be acquired based on the reading, by the sequencer, of a predetermined number of nucleotides from the opposite end of the DNA fragment. In other words, the first sequence data may be a first read of a pair of paired-end reads, and the second sequence data may be a second read of the pair of paired-end reads.

The processor may compare the reference sequence data with the second sequence data to identify the occurrence of a variant in the second sequence data, at S1340. If the occurrence of a variant is identified, the processor may identify a position in the second sequence data and a gene where the variant occurred.

The processor may generate a second report (e.g., an interim report) including the identified variant, and provide the generated second report to the client, at S1350. The second report may be a kind of interim report and may be provided to the client before the final report is completed. The processor may include a false negative rate or a false positive rate for the variant in the second report. In this case, the processor may use at least one of an algorithm or a machine learning model for calculating the false negative rate and/or the false positive rate to calculate the false negative rate or the false positive rate for the variant.

The processor may identify a structural variant by the variant analysis at the third time point. In this case, the third time point may be after reading of the first read of the pair of paired-end reads is completed, and at which the second read of the pair of paired-end reads is partially read. For example, the third time point may be cycle 190. In addition, the structural variant may include variants related to inversion, translocation, deletion, duplication, insertion, etc.

If the variant is analyzed before the third time point (e.g., before the sequence data associated with the second read is aligned), the probability of detecting an existing point mutation is high, but the probability of detecting an existing structural variant due to partial breakage of a chromosome, etc. may be very low. For example, it may be assumed that the sequence data associated with the first read of a pair of paired-end reads is aligned to the first sub-region associated with the first chromosome included in the reference sequence data, and the sequence data associated with the second read of the pair of paired-end reads is aligned to the second sub-region associated with the second chromosome included in the reference sequence data. In this situation, only when the sequence data associated with the first read is aligned in the forward direction in the first sub-region associated with the first chromosome, and the sequence data associated with the second read is aligned in the reverse direction in the second sub-region associated with the second chromosome, it may be determined that normal alignment of the sequence data is performed.

On the other hand, if the direction of the alignment with respect to the sequence data associated with the first read or the second sequence data associated with the second read is different from the above, the processor may identify a structural variant associated with an inversion or duplication based on the abnormally aligned sequence data.

Additionally or alternatively, the processor may identify the structural variants such as inversion, translocation, deletion, duplication, insertion, etc. based on breakpoints caused by these structural variants. For example, if the breakpoints generated due to the structural variants as described above are found in the first read or the second read, the occurrence of the structural variants may be detected. Furthermore, if a breakpoint is found between a position mapped with the first read and a position mapped with the second read, the occurrence of the structural variant may also be detected. For example, when it is assumed that the first read of the pair of paired-end reads is mapped to chromosome 1 and the second read of the pair of paired-end reads is mapped to chromosome 3, the occurrence of a structural variant in which a part of chromosome 3 is translocated to chromosome 1 (or a structural variant in which a part of chromosome 1 is translocated to chromosome 3) may be detected.

As described above, based on the sequence data related to the first read aligned before the third time point and the sequence data associated with the second read aligned at the third time point, the processor may detect the point mutations as well as the structural variants early. That is, existing structural variants may be detected with a high probability at the time of interim analysis.

Meanwhile, in some examples, if the third marking code is acquired at the third time point, the processor may convert the marking data including the plurality of marking codes accumulated from the analysis start time to the third time point into the second sequence data. That is, instead of selecting only the third marking code at the third time point and converting it into a third nucleotide identifier, the processor may convert the marking data including the third marking code accumulated from the analysis start time to the third time point into the second sequence data. In this case, as all the marking codes accumulated at the third time point and included in the marking data are converted into nucleotide identifiers, the second sequence data may be generated. The processor may align the converted second sequence data and identify a variant from the aligned second sequence data.

In addition, if the last cycle (e.g., cycle 300) is performed by the sequencer and the last marking code is acquired, the processor may identify a variant from the third sequence data including the nucleotide identifiers converted in all cycles. In addition, the processor may generate a third report (e.g., a final report) based on the identified variant and provide the generated report to the client.

Meanwhile, target variant or mutation information may be acquired and stored in the information processing system. In this case, the target variant information may include at least one region in the entire region of the sequence data, which needs intensive verification. A table associating disease information (e.g., disease type, etc.) with target variant information may be stored in the information processing system in advance. For example, a first disease (e.g., breast cancer) may be known to have a variant in the first region, in which case the first target variant information including the first region may be associated with the first disease information and stored in the information processing system. As another example, a second disease (e.g., lung cancer) may be known to have a variant in the second region, in which case the second target variant information including the second region may be associated with the second disease information and stored in the information processing system.

The processor may receive, from a client, a potential disease of a test subject (e.g., a patient) from whom a sample is collected, and acquire target variant information corresponding to the disease. In addition, after identifying the region of the sequence data included in the target variant information (that is, the region to be verified), the processor may determine whether or not a variant occurred in the identified region of the aligned sequence data. In addition, the processor may generate a report based on the identified variant and report to the client.

According to some examples, if the target variant information is acquired, the processor may determine a sub-region of the entire reference region which is associated with the target variant information as a region to be verified. In addition, if the sequence data is not aligned to the region to be verified, the processor may determine that the alignment of the sequence data fails. For example, if alignment is attempted on the sequence data, but at least one read included in the sequence data is overlapped and mapped to a sub-region other than the region to be verified, or is not mapped to the region to be verified, the processor may determine that the alignment with respect to the sequence data fails. If the alignment of the sequence data fails, the processor may defer the alignment of the sequence data, and if a predetermined number of nucleotide identifiers are additionally included in the sequence data, the alignment of the sequence data may be attempted again.

If variants are intensively verified in only a designated region where target variant information is used, a report can be generated and reported to the client more quickly. In this case, the client can identify the genetic variant for the test subject's disease, and quickly establish a treatment plan based on the identified genetic variant.

Meanwhile, if the test subject is a cancer patient, the amount of marking data required for analysis may be determined based on the purity of the tumor cells included in the sample and/or the timing of early analysis.

FIG. 14 is a diagram illustrating the amount of data required for early analysis according to the ratio of the amount of DNA extracted from tumor cells to the amount of DNA extracted from non-tumor cells included in the sample. In this case, the non-tumor cells may be cells of normal tissue around the tumor tissue, collected together in the process of collecting the tumor tissue from the test subject, for example.

FIG. 14 illustrates that the unit of the amount of data is a gigabase or a gigabase pair, and the ratio of tumor cells increases from R1 to R5.

Referring to FIG. 14, the amount of data (e.g., the amount of sequence data) of a test subject required for early analysis may be determined based on the ratio (x) of tumor cells in the sample. In FIG. 14, the numbers in parentheses may be the total amounts of data of the test subject to be processed by the sequencer, and the numbers not in parentheses may be the amount of data required for early analysis. In this case, the total amount of data of the test subject may be related to the amount of DNA of the test subject in the sample input to the sequencer. In addition, the amount of data required for early analysis is related to the amount of sequence data of the test subject, and may be the amount of partial sequence data acquired in a specific cycle rather than the total sequence data amount acquired in the entire cycle.

Referring to FIG. 14, if the early analysis cycle (that is, the reporting time point) is cycle and the ratio of tumor cells (x) is less than or equal to R1, the data amount of the test subject corresponding to approximately 900 gigabases may be determined. In this case, the amount of the test subject's data may be the amount of the test subject's DNA sequence data output from the sequencer, and may be proportional to the amount of the test subject's DNA sample input to the sequencer. That is, as the amount of data of the test subject increases, the amount of the test subject's DNA sample input to the sequencer may increase. A DNA library having a DNA sample amount corresponding to the determined data amount of the test subject may be input to the sequencer. That is, a DNA library including a DNA sample in an amount corresponding to 900 gigabases may be input into the sequencer.

In addition, if the early analysis cycle (that is, reporting time point) is cycle 40 and the ratio of tumor cells (x) is less than or equal to R1, the amount of data required for analysis may be determined to be approximately 120 gigabases. That is, if a DNA sample of a test subject in an amount corresponding to a 900 gigabases is processed in the sequencer, sequence data having a size of approximately 120 gigabases may be converted at cycle 40, and the information processing system may identify the variant from the sequence data having the size of approximately 120 gigabases, and generate a first report.

As another example, if the early analysis cycle is cycle 40 and the ratio of tumor cells (x) exceeds R5, the amount of data of the test subject corresponding to approximately 247 gigabases may be determined, and the amount of data required for early analysis may be determined to be approximately 33 gigabases.

Meanwhile, if the early analysis cycle is cycle 190 and the ratio of tumor cells (x) is less than or equal to R1, the amount of data of the test subject corresponding to approximately 160 gigabases may be determined, and the amount of data required for early analysis may be determined to be about 100 gigabases. In this case, after cycle 190 is completed, the information processing system may acquire sequence data having a size of approximately 100 gigabases, identify a variant based on the sequence data, and generate a second report.

As another example, if the early analysis cycle is cycle 190 and the ratio of tumor cells (x) exceeds R5, the amount of data of the test subject corresponding to approximately 44 gigabases may be determined, and the amount of data required for analysis may be determined to be approximately 28 gigabases.

As illustrated in FIG. 14, the higher the purity of the tumor cells, the more reliably variants can be identified, such that the amount of data required for early analysis of the corresponding cycle and the total amount of the test subject's sample input to the sequencer can be reduced. Meanwhile, it is exemplified that the amount of data required for analysis and the amount of data of the test subject input to the early analysis of cycle 190 is relatively small as compared to cycle 40. The reason is that structural variants can be more clearly identified by analyzing the sequence data acquired during 190 cycles, and also the accuracy is higher at cycle 190 than at cycle 40. Meanwhile, the early analysis of cycle 190 requires more time than the early analysis of cycle 40. That is, if a report is desired to be received at an early time point (e.g., when cycle 40 is completed), a DNA library of a relatively large amount is input to the sequencer. Conversely, if the report is desired to be received at a relatively late time point (e.g., when cycle 190 is completed), a DNA library of a relatively small amount is put into the sequencer.

As such, based on the ratio of tumor cells to non-tumor cells and/or the time point of early analysis, the amount of sample to be input to the sequencer and the amount of data required for early analysis may be determined.

Meanwhile, in some examples, if the amount of data required for early analysis and the amount of a sample corresponding to the amount of data are determined, information indicating the determined amount of the sample may be displayed to a user of the information processing system 110 or stored in a storage device accessible by the information processing system 110. In some examples, if the amount of data required for early analysis and the amount of a sample corresponding to the amount of data are determined, information indicating the determined amount of sample may be provided to the sequencer 120. In this case, the sequencer 120 may take an appropriate amount from the entire input sample based on the provided information and perform sequencing, thereby generate data corresponding to the previously determined amount of data.

Figure 15:
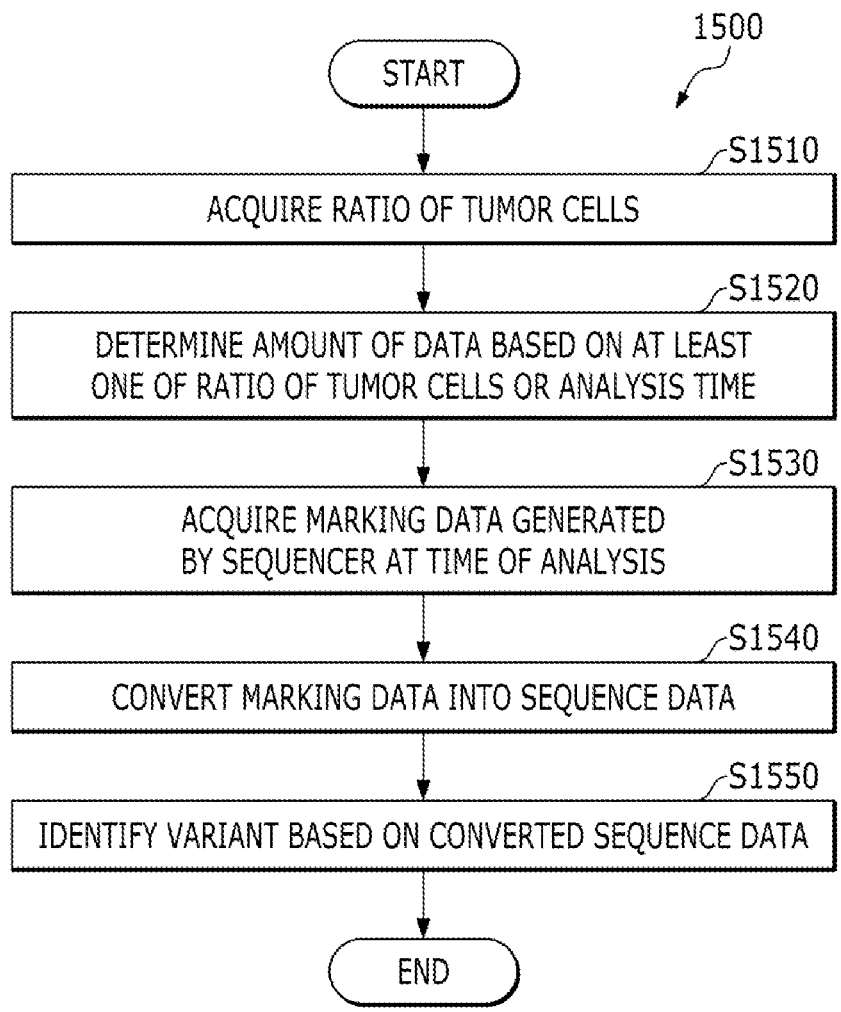
FIG. 15 is a flowchart illustrating a method for determining a target data production amount for sequencing.

FIG. 15 is a flowchart illustrating a method 1500 for analyzing sequences, which determines a target data amount for sequence production. The method illustrated in FIG. 15 is merely one example of achieving the object of the present disclosure, and it is understood that some steps may be added or deleted as necessary. In addition, the method illustrated in FIG. 15 may be performed by one or more processors included in the information processing system. For convenience of description, it will be described that each step illustrated in FIG. 15 is performed by a processor included in the information processing system illustrated in FIG. 1.

First, the processor may acquire a ratio of tumor cells to normal cells included in the sample, at S1510. For example, the ratio of tumor cells may be acquired through a microscope and input into an information processing system. As another example, the ratio of tumor cells may be identified or acquired based on a disease type of a test subject to be tested. The mapping information of each disease type and the ratio of tumor cells may be stored in the information processing system in advance, and the information processing system may acquire the ratio of tumor cells corresponding to the disease type of the test subject provided from the client.

The processor may determine the target data amount to be input to the sequencer for analyzing sequences, based on at least one of a ratio of tumor cells or a desired early analysis time, at S1520. In this case, the early analysis time point is a time point of identifying variants in advance before all cycles are completed to generate an early analysis report, and may be received from the client. In addition, the processor may determine an amount of data required for early analysis based on at least one of a ratio of tumor cells or an early analysis time point. For example, the early analysis time point may include a first analysis time point that identifies a variant based on a first number of marking codes acquired from a first read of the DNA fragment, or a second analysis time point that identifies the variant based on a second number of marking codes acquired from the first read of the DNA fragment and a third number of marking codes acquired from the second read of the DNA fragment.

The amount of the subject's DNA sample corresponding to the determined target data amount to be input may be input to the sequencer, and marking data may be generated by the sequencer. In this case, the amount of the DNA sample of the test subject may be determined based on the determined target data amount to be input, and at least one cartridge including the determined amount of the DNA sample may be loaded into the sequencer.

The processor may acquire the marking data generated by the sequencer at the time of analysis, at S1530. That is, the sequencing operation on the DNA library corresponding to the determined target data amount to be input may be performed by the sequencer and the marking data may be generated. In this case, the amount of the test subject's DNA sample to be input to the sequencer may be determined based on the determined target data amount. The processor may convert the marking data into sequence data, at S1540. In this case, the amount of sequence data may correspond to the target data amount required for analysis determined based on the ratio of tumor cells and/or the time of analysis. The processor may determine the amount of data required for early reporting of the sequence based on at least one of the acquired ratio of tumor cells or the analysis time point. In this case, the size of the converted sequence data may be a size corresponding to the amount of data required for early reporting of the determined sequence.

The processor may identify a variant based on the converted sequence data, at S1550. The processor may provide the client with a report including the identified variant. Accordingly, the report may be provided to the client at the determined time point.

The flowcharts described above and the description provided above are merely examples, and may be implemented differently in some examples. For example, in some examples, the order of respective steps may be changed, some steps may be repeatedly performed, some steps may be omitted, or some steps may be added.

The method described above may be provided as a computer program stored in a computer-readable recording medium for execution on a computer. The medium may be a type of medium that continuously stores a program executable by a computer, or temporarily stores the program for execution or download. In addition, the medium may be a variety of recording means or storage means having a single piece of hardware or a combination of several pieces of hardware, and is not limited to a medium that is directly connected to any computer system, and accordingly, may be present on a network in a distributed manner. An example of the medium includes a medium configured to store program instructions, including a magnetic medium such as a hard disk, a floppy disk, and a magnetic tape, an optical medium such as a CD-ROM and a DVD, a magnetic-optical medium such as a floptical disk, and a ROM, a RAM, a flash memory, and so on. In addition, other examples of the medium may include an app store that distributes applications, a site that supplies or distributes various software, and a recording medium or a storage medium managed by a server.

The methods, operations, or techniques of the present disclosure may be implemented by various means. For example, these techniques may be implemented in hardware, firmware, software, or a combination thereof. Those skilled in the art will further appreciate that various illustrative logical blocks, modules, circuits, and algorithm steps described in connection with the disclosure herein may be implemented in electronic hardware, computer software, or combinations of both. To clearly illustrate this interchangeability of hardware and software, various illustrative components, blocks, modules, circuits, and steps have been described above generally in terms of their functionality. Whether such a function is implemented as hardware or software varies depending on design requirements imposed on the particular application and the overall system. Those skilled in the art may implement the described functions in varying ways for each particular application, but such implementation should not be interpreted as causing a departure from the scope of the present disclosure.

In a hardware implementation, processing units used to perform the techniques may be implemented in one or more ASICs, DSPs, digital signal processing devices (DSPDs), programmable logic devices (PLDs), field programmable gate arrays (FPGAs), processors, controllers, microcontrollers, microprocessors, electronic devices, other electronic units designed to perform the functions described in the present disclosure, computer, or a combination thereof.

Accordingly, various example logic blocks, modules, and circuits described in connection with the present disclosure may be implemented or performed with general purpose processors, DSPs, ASICs, FPGAs or other programmable logic devices, discrete gate or transistor logic, discrete hardware components, or any combination of those designed to perform the functions described herein. The general purpose processor may be a microprocessor, but in the alternative, the processor may be any related processor, controller, microcontroller, or state machine. The processor may also be implemented as a combination of computing devices, for example, a DSP and microprocessor, a plurality of microprocessors, one or more microprocessors associated with a DSP core, or any other combination of the configurations.

In the implementation using firmware and/or software, the techniques may be implemented with instructions stored on a computer-readable medium, such as random access memory (RAM), read-only memory (ROM), non-volatile random access memory (NVRAM), programmable read-only memory (PROM), erasable programmable read-only memory (EPROM), electrically erasable PROM (EEPROM), flash memory, compact disc (CD), magnetic or marking data storage devices, etc. The instructions may be executable by one or more processors, and may cause the processor(s) to perform certain aspects of the functions described in the present disclosure.

If implemented in software, the techniques described above may be stored on a computer-readable medium as one or more instructions or codes, or may be transmitted through a computer-readable medium. The computer-readable media include both the computer storage media and the communication media including any medium that facilitates the transmission of a computer program from one place to another. The storage media may also be any available media that may be accessed by a computer. By way of non-limiting example, such a computer-readable medium may include RAM, ROM, EEPROM, CD-ROM or other optical disk storage, magnetic disk storage or other magnetic storage devices, or any other media that can be used to transmit or store desired program code in the form of instructions or data structures and can be accessed by a computer. In addition, any connection is properly referred to as a computer-readable medium.

For example, if the software is transmitted from a website, server, or other remote sources using coaxial cable, fiber optic cable, twisted pair, digital subscriber line (DSL), or wireless technologies such as infrared, wireless, and microwave, the coaxial cable, the fiber optic cable, the twisted pair, the digital subscriber line, or the wireless technologies such as infrared, wireless, and microwave are included within the definition of the medium. The disks and the discs used herein include CDs, laser disks, optical disks, digital versatile discs (DVDs), floppy disks, and Blu-ray disks, where disks usually magnetically reproduce data, while discs optically reproduce data using a laser. The combinations described above should also be included within the scope of the computer-readable media.

The software module may reside in RAM memory, flash memory, ROM memory, EPROM memory, EEPROM memory, registers, hard disk, removable disk, CD-ROM, or any other form of storage medium known. An exemplary storage medium may be connected to the processor, such that the processor may read or write information from or to the storage medium. Alternatively, the storage medium may be integrated into the processor. The processor and the storage medium may exist in the ASIC. The ASIC may exist in the user terminal. Alternatively, the processor and storage medium may exist as separate components in the user terminal.

Although the examples described above have been described as utilizing aspects of the currently disclosed subject matter in one or more standalone computer systems, aspects are not limited thereto, and may be implemented in conjunction with any computing environment, such as a network or distributed computing environment. Furthermore, the aspects of the subject matter in the present disclosure may be implemented in multiple processing chips or devices, and storage may be similarly influenced across a plurality of devices. Such devices may include PCs, network servers, and portable devices.

Although the present disclosure has been described in connection with some examples herein, various modifications and changes can be made without departing from the scope of the present disclosure, which can be understood by those skilled in the art to which the present disclosure pertains. In addition, such modifications and changes should be considered within the scope of the claims appended herein.

The invention claimed is:

1. A method performed by one or more processors, the method comprising:
   determining, for a partial genome sequencing process of an organism, at least one target length of at least one partial genome sequence output;
   causing a sequencer to generate, based on a sample of the organism, a plurality of marking data associated with a genome of the organism, wherein generating of the plurality of marking data comprises:
      imaging first marking data of the plurality of marking data;
   determining, based on a plurality of cycles associated with the at least one target length, the first marking data of the plurality of marking data, wherein the first marking data comprises a plurality of image data portions, and wherein the plurality of image data portions comprises:
      a first image data portion associated with a first length of a first polynucleotide chain of the genome; and
      a second image data portion associated with a second length of a second polynucleotide chain of the genome, wherein the second length is shorter than the first length; and
   before imaging second marking data of the plurality of marking data:
      converting the first marking data to first sequence data;
      detecting, based on the first sequence data, completion of a first read of paired-end reads and a partial completion of a second read of the paired-end reads, wherein the partial completion of the second read is associated with the second length of the second polynucleotide chain and satisfies a target length associated with the second read;
aligning, based on reference sequence data associated with the organism, the first sequence data, wherein the aligned first sequence data comprises:
a first aligned portion corresponding to the first read; and
a second aligned portion corresponding to a partial portion of the second read;
identifying, based on the aligned first sequence data, a structural variant; and
generating a first report comprising information on the identified structural variant.

2. The method according to claim 1, further comprising:
before imaging the first marking data, receiving prior marking data; and
before the aligning the first sequence data:
aligning, based on the reference sequence data, prior sequence data, wherein the prior sequence data is generated based on the prior marking data, and wherein the prior marking data comprises an image data portion associated with a length of the first polynucleotide chain that is shorter than the first length of the first polynucleotide chain;
identifying, based on the aligned prior sequence data, a point mutation; and
generating a report comprising information on the identified point mutation.

3. The method according to claim 1, further comprising:
before the generating the first report, identifying, based on the aligned first sequence data, a point mutation,
wherein the first report further comprises information on the identified point mutation.

4. The method according to claim 1, further comprising:
identifying the first image data portion and the second image data portion; and
generating an image file comprising the first marking data.

5. The method according to claim 1, further comprising:
before the aligning the first sequence data,
determining a target data amount for sequence production; and
acquiring the first sequence data, wherein the first sequence data is generated by the sequencer inputted with an amount of a determined sample corresponding to the determined target data amount.

6. The method according to claim 5, wherein the determining the target data amount comprises:
acquiring a ratio of tumor cells included in the determined sample to non-tumor cells included in the determined sample; and
determining, based on the acquired ratio, the target data amount.

7. The method according to claim 6, wherein the acquiring the ratio comprises:
identifying, based on a disease type of a test subject, the ratio.

8. The method according to claim 5, wherein the determined target data amount is an amount of data required for early reporting of a variant identification result, and
wherein a size of the acquired first sequence data is a size corresponding to the determined target data amount.

9. The method according to claim 5, further comprising:
after the determining the target data amount, outputting the amount of the determined sample corresponding to the determined target data amount.

10. The method according to claim 1, further comprising:
before the aligning the first sequence data,
aligning, based on the reference sequence data, prior sequence data wherein the prior sequence data is generated based on prior marking data, and wherein the prior marking data comprises an image data portion associated with a length of the first polynucleotide chain that is shorter than the first length of the first polynucleotide chain; and
determining, based on a failure associated with the aligning the prior sequence data, an alignment operation associated with the first sequence data.

11. The method according to claim 10, wherein the reference sequence data comprises a plurality of sub-regions, and
wherein the method further comprises:
calculating an alignment ratio, wherein the alignment ratio comprises a ratio of deoxyribonucleic acid (DNA) reads uniquely aligned to one sub-region of the plurality of sub-regions to DNA reads included in the prior sequence data; and
based on the calculated alignment ratio being less than a target alignment ratio, determining the failure associated with the aligning the prior sequence data.

12. The method according to claim 10, further comprising:
after the determining the failure, retrying an alignment of the prior sequence data,
wherein the retrying the alignment of the prior sequence data is based on:
additional nucleotide identifiers being added to the prior sequence data; and
a number of the additional nucleotide identifiers added to the prior sequence data satisfying a predetermined threshold number.

13. The method according to claim 10, further comprising:
before the aligning the prior sequence data,
acquiring target variant information; and
determining, from an entire region associated with the reference sequence data, a sub-region associated with the target variant information,
wherein the determining the alignment operation associated with the first sequence data is based on a determination that the prior sequence data is not mapped to the determined sub-region.

14. The method according to claim 13, wherein the acquiring the target variant information comprises acquiring, based on disease information of a test subject, the target variant information.

15. The method according to claim 1, further comprising:
after imaging the plurality of marking data and converting the imaged plurality of marking data to whole sequence data, analyzing a whole genome sequencing result.

16. The method according to claim 1, wherein the target length associated with the second read is determined for detecting at least one structural variant different from point mutations.

17. The method according to claim 1, wherein the structural variant comprises at least one of:
a structural variant associated with inversion;
a structural variant associated with translocation; or
a structural variant associated with duplication.

18. A computer-readable non-transitory recording medium storing instructions that, when executed, cause:
determining, for a partial genome sequencing process of an organism, at least one target length of at least one partial genome sequence output;

causing a sequencer to generate, based on a sample of the organism, a plurality of marking data associated with a genome of the organism, wherein generating of the plurality of marking data comprises:
  imaging first marking data of the plurality of marking data;
determining, based on a plurality of cycles associated with the at least one target length, the first marking data of the plurality of marking data, wherein the first marking data comprises a plurality of image data portions, and wherein the plurality of image data portions comprises:
  a first image data portion associated with a first length of a first polynucleotide chain of the genome; and
  a second image data portion associated with a second length of a second polynucleotide chain of the genome, wherein the second length is shorter than the first length; and
before imaging second marking data of the plurality of marking data:
  converting the first marking data to first sequence data;
  detecting, based on the first sequence data, completion of a first read of paired-end reads and a partial completion of a second read of the paired-end reads, wherein the partial completion of the second read is associated with the second length of the second polynucleotide chain and satisfies a target length associated with the second read;
  aligning, based on reference sequence data associated with the organism, the first sequence data, wherein the aligned first sequence data comprises:
    a first aligned portion corresponding to the first read; and
    a second aligned portion corresponding to a partial portion of the second read;
  identifying, based on the aligned first sequence data, a structural variant; and
  generating a first report comprising information on the identified structural variant.

19. A system comprising:
at least one processor; and
memory storing instructions that, when executed by the at least one processor, cause the system to:
  determine, for a partial genome sequencing process of an organism, at least one target length of at least one partial genome sequence output;
  cause a sequencer to generate, based on a sample of the organism, a plurality of marking data associated with a genome of the organism, wherein generating of the plurality of marking data comprises:
    imaging first marking data of the plurality of marking data;
  determine, based on a plurality of cycles associated with the at least one target length, the first marking data of the plurality of marking data, wherein the first marking data comprises a plurality of image data portions, and wherein the plurality of image data portions comprises:
    a first image data portion associated with a first length of a first polynucleotide chain of the genome; and
    a second image data portion associated with a second length of a second polynucleotide chain of the genome, wherein the second length is shorter than the first length; and
  before imaging second marking data of the plurality of marking data:
    convert the first marking data to first sequence data;
    detect, based on the first sequence data, completion of a first read of paired-end reads and a partial completion of a second read of the paired-end reads, wherein the partial completion of the second read is associated with the second length of the second polynucleotide chain and satisfies a target length associated with the second read;
    align, based on reference sequence data associated with the organism, the first sequence data, wherein the aligned first sequence data comprises:
      a first aligned portion corresponding to the first read; and
      a second aligned portion corresponding to a partial portion of the second read;
    identify, based on the aligned first sequence data, a structural variant; and
    generate a first report comprising information on the identified structural variant.

20. The system according to claim 19, wherein the structural variant comprises at least one of:
a structural variant associated with inversion;
a structural variant associated with translocation; or
a structural variant associated with duplication, and
wherein the instructions, when executed by the at least one processor, cause the system to determine the target length associated with the second read for detecting at least one structural variant different from point mutations.

* * * * *